United States Patent
Eriksson et al.

(10) Patent No.: US 11,000,427 B2
(45) Date of Patent: May 11, 2021

(54) DISPOSABLE PANT-TYPE ABSORBENT ARTICLE WITH A LEG CUFF

(71) Applicant: SCA Hygiene Products AB, Gothenburg (SE)

(72) Inventors: Katarina Eriksson, Gothenburg (SE); Lucas Bäck, Gothenburg (SE); Anna Klinte Olsson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 370 days.

(21) Appl. No.: 15/744,120

(22) PCT Filed: Sep. 9, 2015

(86) PCT No.: PCT/SE2015/050950
§ 371 (c)(1),
(2) Date: Jan. 12, 2018

(87) PCT Pub. No.: WO2017/044022
PCT Pub. Date: Mar. 16, 2017

(65) Prior Publication Data
US 2018/0200121 A1 Jul. 19, 2018

(51) Int. Cl.
*A61F 13/496* (2006.01)
*A61F 13/49* (2006.01)
(Continued)

(52) U.S. Cl.
CPC ...... *A61F 13/496* (2013.01); *A61F 13/15593* (2013.01); *A61F 13/49011* (2013.01);
(Continued)

(58) Field of Classification Search
CPC ...... A61F 2013/49033; A61F 13/49009; A61F 13/496; A61F 13/49019; A61F 13/15593;
(Continued)

(56) References Cited

U.S. PATENT DOCUMENTS 5,735,839 A 4/1998 Kawaguchi et al.
5,827,253 A 10/1998 Young et al.
(Continued)

FOREIGN PATENT DOCUMENTS

CN 1316893 A 10/2001
CN 1345576 A 4/2002
(Continued)

OTHER PUBLICATIONS

Office Action dated Aug. 12, 2019, by the Colombian Patent Office in corresponding Colombian Patent Application No. NC2018/0002745, and an English Translation of the Office Action. (17 pages).

(Continued)

*Primary Examiner* — Ophelia A Hawthorne
*Assistant Examiner* — Heather K Barnwell
(74) *Attorney, Agent, or Firm* — Buchanan Ingersoll & Rooney PC

(57) ABSTRACT

A disposable pant-type absorbent article includes a chassis and an absorbent body. The chassis has a front portion and a back portion and each of the front and back portions has a waist edge, a pair of leg edges and a pair of side edges. The front and back portions are joined to each other at opposite side edges to at least partly define a waist-opening and a pair of leg-openings. The absorbent body is located mainly in a crotch portion of the article. An elastic leg feature is fastened to the chassis at least partly along leg edges. The elastic leg feature extends from the associated side edge towards a centre line in the longitudinal direction of the article. The disclosure also relates to a corresponding method of manufacturing a pant-type absorbent article, as well as an array of gender-specific, disposable, absorbent articles.

21 Claims, 8 Drawing Sheets

(51) Int. Cl.
*A61F 13/494* (2006.01)
*A61F 13/15* (2006.01)

(52) U.S. Cl.
CPC .. *A61F 13/49017* (2013.01); *A61F 13/49019* (2013.01); *A61F 13/494* (2013.01); *A61F 2013/49026* (2013.01)

(58) Field of Classification Search
CPC .. A61F 2013/49038; A61F 2013/49026; A61F 13/49017; A61F 13/49011; A61F 13/494; A61F 13/15; A61F 13/49; A61F 13/64
See application file for complete search history.

(56) References Cited

U.S. PATENT DOCUMENTS

| | | | |
|---|---|---|---|
| 6,083,210 | A | 7/2000 | Young et al. |
| 6,767,343 | B2 | 7/2004 | Shimada et al. |
| 7,632,259 | B2 | 12/2009 | Elfstrom et al. |
| 9,301,881 | B2 | 4/2016 | Ando et al. |
| 2004/0133180 | A1 | 7/2004 | Mori et al. |
| 2005/0137563 | A1 | 6/2005 | Van Gompel et al. |
| 2007/0118088 | A1 | 5/2007 | LaVon et al. |
| 2008/0275415 | A1 | 11/2008 | Wheeler et al. |
| 2010/0106123 | A1* | 4/2010 | Fukae ............... A61F 13/49012 604/373 |
| 2010/0108554 | A1 | 5/2010 | Melius et al. |
| 2010/0191212 | A1* | 7/2010 | Torigoshi .......... A61F 13/49014 604/385.23 |
| 2011/0094661 | A1* | 4/2011 | Thorson ............ A61F 13/15585 156/211 |
| 2011/0251576 | A1 | 10/2011 | Ando et al. |
| 2012/0086145 | A1 | 4/2012 | Nakamura et al. |
| 2013/0060219 | A1* | 3/2013 | Mukai ............... A61F 13/49058 604/385.3 |
| 2013/0277154 | A1 | 10/2013 | Fritz et al. |
| 2013/0281957 | A1 | 10/2013 | Fritz et al. |
| 2014/0288521 | A1 | 9/2014 | Wade et al. |
| 2014/0288523 | A1 | 9/2014 | Hasse et al. |
| 2015/0328056 | A1 | 11/2015 | Een et al. |

FOREIGN PATENT DOCUMENTS

| | | |
|---|---|---|
| CN | 101621977 A | 1/2010 |
| CN | 102574389 A | 7/2012 |
| CO | 04-097204 | 2/2006 |
| CO | 08-074660 | 11/2008 |
| CO | 08-117263 | 2/2010 |
| EP | 0241925 | 10/1987 |
| EP | 532005 A1 | 3/1993 |
| EP | 748197 B1 | 7/1999 |
| EP | 1 354 576 A1 | 10/2003 |
| EP | 1 374 814 A1 | 1/2004 |
| EP | 1448133 A2 | 8/2004 |
| EP | 2 123 241 A1 | 11/2009 |
| EP | 2123241 A1 | 11/2009 |
| EP | 2 415 430 A1 | 2/2012 |
| EP | 2561846 | 2/2013 |
| EP | 2 656 825 A1 | 10/2013 |
| EP | 2656825 A1 | 10/2013 |
| JP | H06-000421 | 1/1994 |
| JP | H10-127687 | 5/1998 |
| JP | H11-99165 | 4/1999 |
| JP | 2002-035028 A | 2/2002 |
| JP | 2002-159529 A | 6/2002 |
| JP | 2002-172132 A | 6/2002 |
| JP | 2010-051345 | 3/2010 |
| JP | 2010-227654 | 10/2010 |
| JP | 2012-050883 | 3/2012 |
| JP | 2015-066008 | 4/2015 |
| RU | 2397743 C2 | 8/2010 |
| RU | 2506066 C2 | 2/2014 |
| WO | WO 1996/011657 A1 | 4/1996 |
| WO | 0002511 A1 | 1/2000 |
| WO | 03039420 A2 | 5/2003 |
| WO | WO 2014/098683 A1 | 6/2014 |
| ZA | 9803401 B | 10/1998 |

OTHER PUBLICATIONS

Decision to Grant issued in corresponding Russian Patent Application No. 2018112258, dated Apr. 29, 2019 (18 pages).
Notice of Reasons for Rejection issued in corresponding Japanese Patent Application No. 2018-512625, dated Jan. 27, 2020, with English translation (14 pages).
Office Action and Search Report dated Dec. 17, 2018, by the Russian Patent Office in corresponding Russian Patent Application No. 2018112258/12 (019144), and an English Translation of the Office Action. (10 pages).
Notice of Reasons for Rejection issued in corresponding Japanese Patent Application No. 2018-512625, dated Mar. 18, 2019, with English Translation (12 pages).
Office Action dated Aug. 10, 2018, by the Australian Patent Office in corresponding Australian Patent Application No. 2015408538. (8 pages).
International Search Report (PCT/ISA/210) dated May 25, 2016, by the Swedish Patent and Registration Office as the International Searching Authority for International Application No. PCT/SE2015/050950.
Written Opinion (PCT/ISA/237) dated May 25, 2016, by the Swedish Patent and Registration Office as the International Searching Authority for International Application No. PCT/SE2015/050950.
Written Opinion (PCT/IPEA/408) dated Aug. 1, 2017, by the European Patent Office as the International Preliminary Examining Authority for International Application No. PCT/SE2015/050950.
Written Opinion (PCT/IPEA/408) dated Oct. 6, 2017, by the European Patent Office as the International Preliminary Examining Authority for International Application No. PCT/SE2015/050950.
International Preliminary Report on Patentability (PCT/IPEA/409) dated Dec. 12, 2017, by the European Patent Office as the International Preliminary Examining Authority for International Application No. PCT/SE2015/050950.
Extended European Search Report issued in corresponding European Patent Application No. 15903703.5, dated Apr. 8, 2019 (7 pages).
Office Action (Communication) dated Mar. 31, 2020, by the European Patent Office in corresponding European Patent Application No. 15 903 703.5. (6 pages).
Search Report and Written Opinion dated Mar. 14, 2020, by the Brazilian Patent Office in corresponding Brazilian Application No. BR112018003435-5. (4 pages).
Office Action (Notification of the First Office Action) dated May 8, 2020, by the Chinese Patent Office in corresponding Chinese Patent Application No. 201580083854.3, and an English Translation of the Office Action. (18 pages).
Office Action (Communication) dated Sep. 10, 2020, by the European Patent Office in corresponding European Patent Application No. 15 903 703.5. (5 pages).
Decision on Rejection issued in corresponding Japanese Patent Application No. 2018-512625, dated Sep. 28, 2020, with English Translation, 6 pages.
2nd Office Action issued in corresponding Chinese Patent Application No. 20158008854.3, dated Dec. 16, 2020, with English Translation, 11 pages.

* cited by examiner

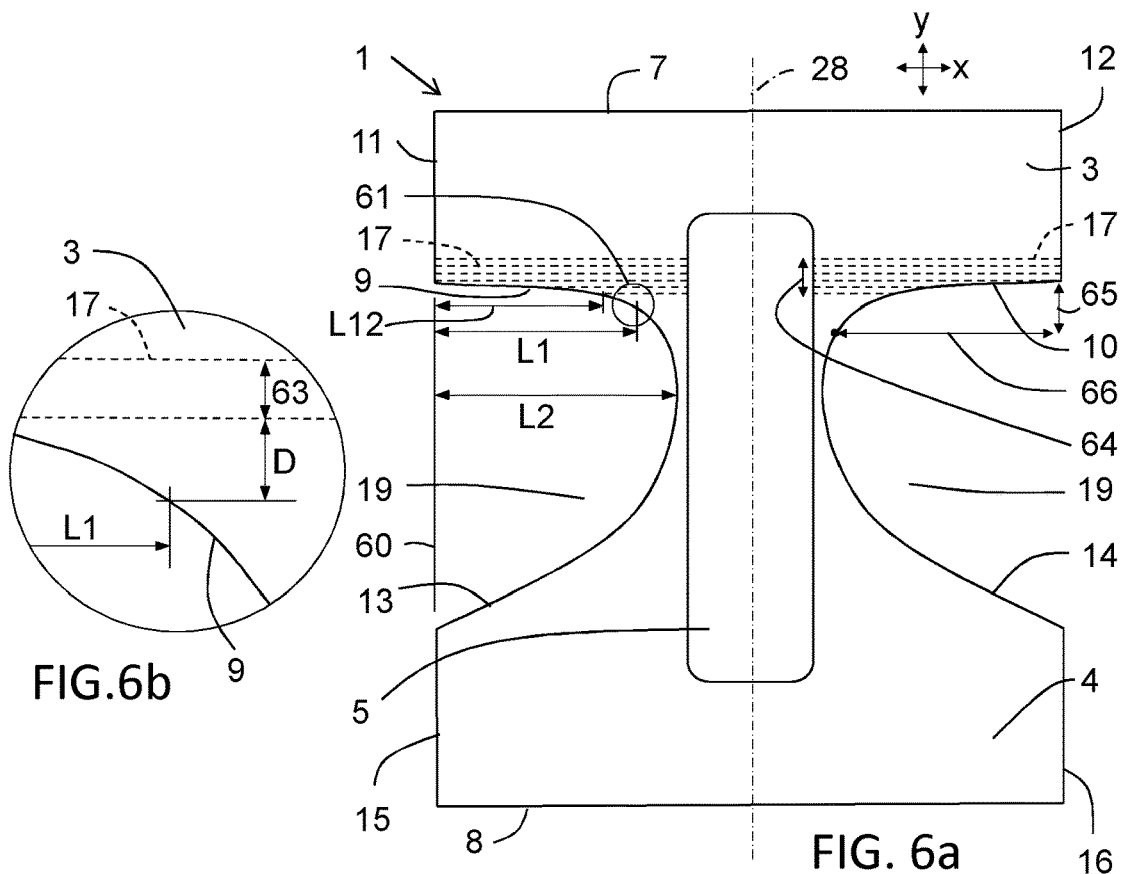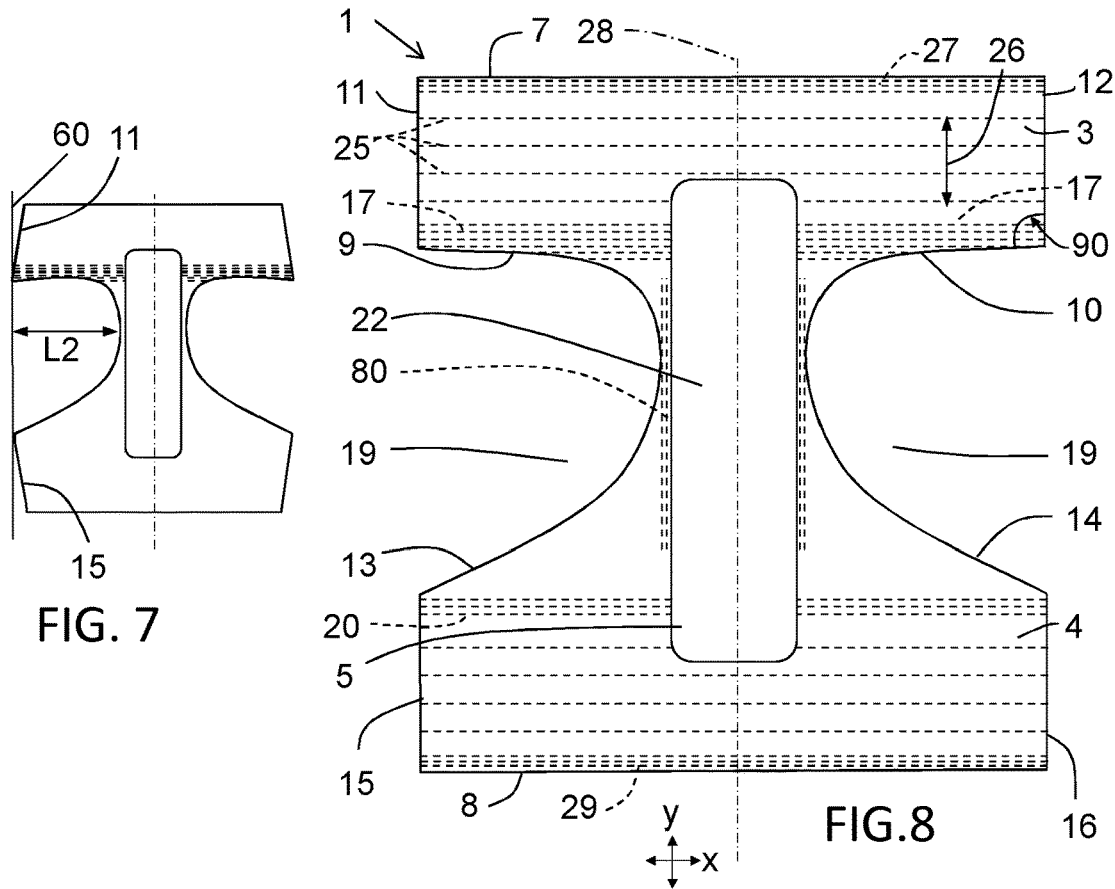

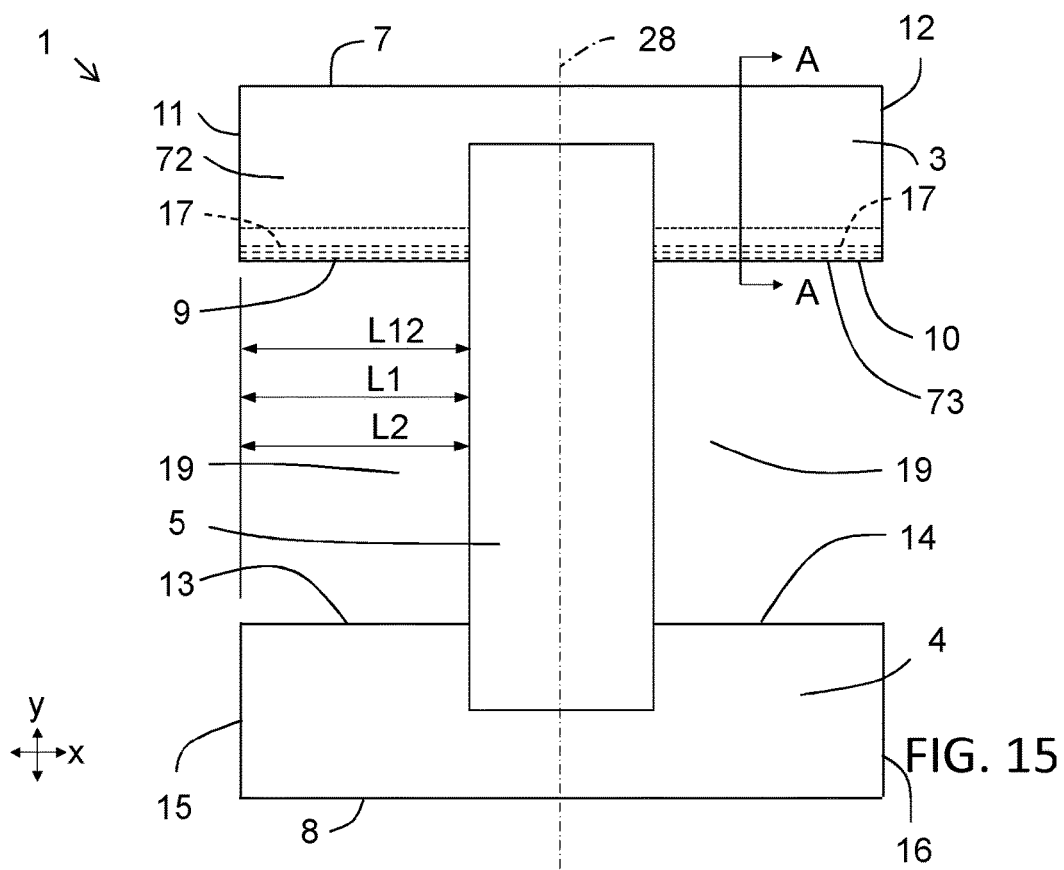
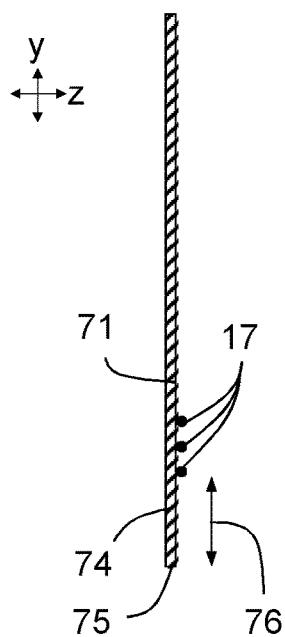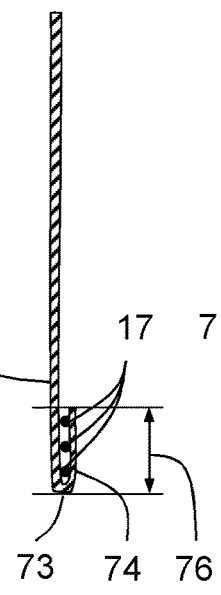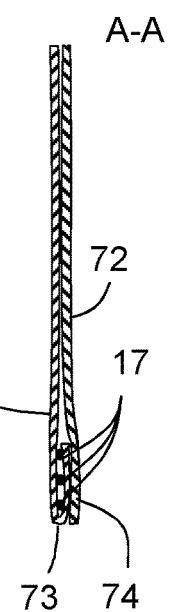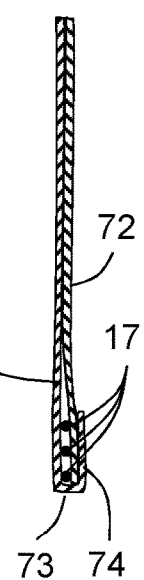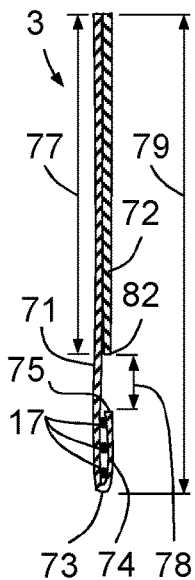

DISPOSABLE PANT-TYPE ABSORBENT ARTICLE WITH A LEG CUFF

TECHNICAL FIELD

This disclosure relates to a disposable pant-type absorbent article, such as a pant diaper, a sanitary pant or incontinence pant. The article comprises a chassis and an absorbent body, wherein the chassis has a front portion and a back portion, each of the front and back portions has a waist edge, a pair of leg edges and a pair of side edges. The front and back portions are joined to each other at opposite side edges to at least partly define a waist-opening and a pair of leg-openings. The absorbent body is located mainly in a crotch portion of the article and an elastic leg feature is fastened to the chassis at least partly along leg edges. The disclosure also relates to a method for manufacturing such a disposable pant-type absorbent articles, as well as an array of gender-specific, disposable, absorbent articles. The disposable pant-type absorbent article is configured for being used by babies, children or adults and may be provided in various sizes.

BACKGROUND

There is general desire in the field of disposable pant-type absorbent articles to provide absorbent articles with increased comfort and fit and that provides the user with confidence with respect to its leakage protection. Document US 2005/0137563 describes a solution for reducing waste of materials while providing undergarments with elastic elements that fit the curve of the leg opening to provide additional reinforcement during use.

While the known disposable absorbent garment is satisfactory for its intended use, such a disposable absorbent garment is nonetheless susceptible to improvement.

SUMMARY

An object of the present disclosure is to provide a disposable pant-type absorbent article with increased comfort and fit and that provides the user with confidence with respect to its leakage protection. This object is at least partly achieved by the features of claim 1.

The disclosure concerns a disposable pant-type absorbent article such as a pant diaper, a sanitary pant or incontinence pant, said article comprises
  a chassis;
  an absorbent body;
  wherein the chassis has a front portion and a back portion, each of the front and back portions has a waist edge, a pair of leg edges and a pair of side edges;
  wherein the front and back portions are joined to each other at opposite side edges to at least partly define a waist-opening (18) and a pair of leg-openings,
  wherein the absorbent body is located mainly in a crotch portion of the article,
  wherein an elastic leg feature is fastened to the chassis at least partly along leg edges, and
  wherein said article has a longitudinal direction and a transverse direction.
  The disclosure is characterised in that:
  the elastic leg feature extends from the associated side edge towards a centre line in the longitudinal direction of the article,
  a portion of the leg elastic feature starting from the side edge has a first length, in which a distance between any point of each leg edge to the nearest part of the elastic leg feature, in a longitudinal direction, is less than 6 millimetres, specifically less than 5 millimetres, and more specifically less than 4 millimetres, and in that the first length is at least 55% of a maximal length of the leg opening in the transverse direction, as measured in an extended state of the absorbent article.

Large frills at the leg edge may be sensed as uncomfortable by a user and perceived by a user as rendering the absorbent article less secure against leakage. Having the elastic leg feature positioned closer to the leg edge may also results in an absorbent article having an improved fit to the shape of the legs of the user. It is thus desirable to provide an elasticised leg edge of the front and/or back portion that has a more cuff-like appearance, thereby providing the disposable absorbent article with an appearance and comfort more similar to cloth underwear.

A pant-type absorbent article has an elastic leg feature mounted close to the leg edge of the chassis and extending over a significant portion of the leg edge, thereby providing the absorbent article with a more cuff-like leg edge that enables improved comfort, fit and deemed leakage protection.

The object of the present disclosure is also at least partly achieved by the features of method for manufacturing a disposable pant-type absorbent article, such as a pant diaper, a sanitary pant or incontinence pant, wherein the method comprising:
  forming a chassis from at least one continuous web material, the chassis has a front portion and a back portion, each of the front and back portions has a waist edge, a pair of leg edges, a pair of side edges, wherein an elastic leg feature is fastened to the chassis at least partly along leg edges, the elastic leg feature extends from the associated side edge towards a centre line in the longitudinal direction of the article, wherein a portion of the leg elastic feature starting from the side edge has a first length, in which a distance between any point of each leg edge to the nearest part of the elastic leg feature, in a longitudinal direction, is less than 6 millimetres, specifically less than 5 millimetres, and more specifically less than 4 millimetres, and wherein the first length is at last 55% of a maximal length of the leg opening in the transverse direction, as measured in an extended state of the absorbent article;
  joining an absorbent body to the chassis such as to be located mainly in a crotch portion of the article; and
  joining the front and back portions to each other at opposite side edges to at least partly define a waist-opening and a pair of leg-openings.

An array of gender-specific, disposable, absorbent articles, comprises:
  a package of first disposable absorbent articles as described in the present disclosure, the package bearing indicia indicating that the articles therein are adapted to be worn by females, each first disposable absorbent article having a first elastic leg feature;
  a package of second disposable absorbent articles as described in this disclosure, the package bearing indicia indicating that the articles therein are adapted to be worn by males, each second disposable absorbent article having a second elastic leg feature;
  wherein the width of the first elastic leg feature is smaller than the width of the second elastic leg feature.

The object of the present disclosure is also at least partly achieved by the features of claim 30, which defines an array of gender-specific, disposable, absorbent articles, wherein the array comprising:

a package of first disposable absorbent articles as described in the present disclosure, the package bearing indicia indicating that the articles therein are adapted to be worn by females, each first disposable absorbent article having a first elastic waist feature;

a package of second disposable absorbent articles as described in this disclosure, the package bearing indicia indicating that the articles therein are adapted to be worn by males, each second disposable absorbent article having a second elastic waist feature;

wherein the width of the first elastic waist feature is smaller than the width of the second elastic waist feature.

The array of gender-specific, disposable, absorbent articles enables the elastic leg feature of the absorbent articles to be adapted more specifically to the anatomy of each gender, such that the pant-type absorbent article may benefit from increased comfort and fit.

Further advantages are achieved by implementing one or several of the features of the dependent claims.

According to an example embodiment of the disclosure, the first length is at least 5 centimetres, specifically at least 10 centimetres, and more specifically at least 15 centimetres in the transverse direction, starting from the side edge, as measured in an extended state of the absorbent article. This length of the leg elastic features may be deemed satisfactory for rendering the absorbent product more comfortable and with improved fit.

According to a further example embodiment of the disclosure, the first length is at least 60%, specifically at least 70%, at more specifically at least 80% of the maximal length of the leg opening in the transverse direction, as measured in an extended state of the absorbent article. This length of the leg elastic features may be deemed satisfactory for rendering the absorbent product more comfortable and with improved fit.

According to a further example embodiment of the disclosure, the absorbent article comprises a second length, which is defined by the maximal length in the transverse direction from the side edge to a point along the periphery of the leg edge having a cut leg elastic feature, wherein the second length is at least 30%, specifically at least 40%, and more specifically at least 50% of a maximal length of the leg opening in the transverse direction, as measured in an extended state of the absorbent article. The relationship provides a length of the leg elastic features deemed satisfactory for rendering the absorbent product more comfortable and with improved fit According to a further example embodiment of the disclosure, the direction of orientation of the elastic leg feature deviates less than 30 degrees, specifically less than 20 degrees, and more specifically less than 10 degrees from the transverse direction over the entire length of the elastic leg feature, as measured in an extended state of the absorbent article. A relatively small deviation of the direction of orientation of the elastic leg feature allows a use of cost-efficient and high-speed manufacturing process.

According to a further example embodiment of the disclosure, the direction of orientation of the elastic leg feature in the front portion deviates less than 7 degrees, specifically less than 5 degrees, and more specifically less than 3 degrees from the transverse direction over the entire length of the elastic leg feature, as measured in an extended state of the absorbent article. A substantially parallel extension of the elastic leg feature in the front portion allows a use of a particularly cost-efficient and high-speed manufacturing process.

According to a further example embodiment of the disclosure, a width of elastic leg feature is from 3 to 60 millimetres, specifically 8 to 40 millimetres, and more specifically 15 to 28 millimetres, as measured in an extended state of the absorbent article. This distance enables cutting of a portion of the elastic leg feature while maintaining a satisfactory elasticity and strength of the remaining portion of the elastic leg feature. The width of elastic leg feature is herein measured in a width direction of the elastic leg feature, which width direction is perpendicular to the longitudinal direction of the elastic leg feature at the point of measurement.

According to a further example embodiment of the disclosure, a width of elastic leg feature varies along the length of the elastic leg feature, specifically along the first length of the elastic leg feature starting from the side edge, as measured in an extended state of the absorbent article. This width of the elastic band enables cutting of a portion of the band while maintaining a satisfactory elasticity and strength of the remaining portion of the band. The width of elastic leg feature is herein measured in a width direction of the elastic leg feature, which width direction is perpendicular to the longitudinal direction of the elastic leg feature at the point of measurement.

According to a further example embodiment of the disclosure, the elastic leg feature comprises a set of 3 to 10 individual elastic threads, specifically 4 to 8 individual elastic threads, or more specifically 5 to 7 individual elastic threads. This number of threads enables cutting of a few elastic threads while maintaining a satisfactory elasticity and strength of the remaining elastic leg feature.

According to a further example embodiment of the disclosure, at least a significant portion, or all, of the individual elastic threads of the elastic leg feature are placed parallel to each other and with a gap of 1 to 6 millimetres between neighbouring threads, as measured in an extended state of the absorbent article. This level of gap is deemed satisfactory for providing a satisfactory elasticity and strength of the elastic leg feature in the finished absorbent article.

According to a further example embodiment of the disclosure, the elastic leg feature comprises an elastic band.

According to a further example embodiment of the disclosure, at least the front and/or back portion is extensively made of an elastic web material, wherein the elastic web material is made of at least two substantially inelastic sheets of web material that are laminated together and having an elastic feature sandwiched between said at least two sheets of web material, and wherein the elastic feature is attached to the at least two sheets in a tensioned state in the transverse direction to provide a web material that is elasticized in the transverse direction. This type of elastic web material may be manufactured cost-efficient and with high speed.

According to a further example embodiment of the disclosure, an elastic waist feature is fastened to the chassis along the waist edge of the front and back portions, the elastic waist feature of the front and back portions extends in a transverse direction substantially parallel with each waist edge. An elastic waist features renders the absorbent article more undergarment-like and results in improved comfort and fit.

According to a further example embodiment of the disclosure, at least one of the front and back portions has a stronger elasticity in a region of the waist edge and/or leg edge than in a centre region of the front and back portion. This results in an absorbent article having improved comfort and fit.

According to a further example embodiment of the disclosure, the chassis is cut such that an initial direction of orientation of the leg edge, starting from the side edge, deviates from the transverse direction towards the closest waist edge, such that an acute angle between the longitudinal direction and the initial direction of orientation of the leg edge near the side edge is formed, as measured in an extended state of the absorbent article. This form of the chassis results in low wear on the cutting equipment while allowing a high amount of the elastic leg feature to be located close or at the leg edge with no or only little inclination of the elastic leg feature with respect to the transverse direction.

According to a further example embodiment of the disclosure, at least one individual elastic thread of the elastic leg feature is at least 3 centimetres, specifically at least 5 centimetres, and more specifically at least 7 centimetres shorter than another individual elastic thread of said elastic leg feature, as measured in an extended state of the absorbent article. This allows close position of the elastic web feature to the leg edge without necessarily having the leg edge and elastic leg feature running in parallel, such that the manufacturing process may be simplified.

According to a further example embodiment of the disclosure, at least one individual elastic thread of the elastic leg feature is cut off during cutting of the leg edge of the chassis. This allows close position of the elastic web feature to the leg edge without necessarily having the leg edge and elastic leg feature running in parallel, such that the manufacturing process may be simplified.

According to a further example embodiment of the disclosure, the number of individual elastic threads of the elastic leg feature varies along the length of the elastic leg feature. This allows close position of the elastic web feature to the leg edge without necessarily having the leg edge and elastic leg feature running in parallel, such that the manufacturing process may be simplified.

According to a further example embodiment of the disclosure, at least part of the band is cut off during cutting of the leg edge of the chassis. This allows close position of the elastic web feature to the leg edge without necessarily having the leg edge and elastic leg feature running in parallel, such that the manufacturing process may be simplified.

According to a further example embodiment of the disclosure, a length of the leg edge in the longitudinal direction is less than 50%, specifically less than 35%, and more specifically less than 20% of a length of the leg edge in the transverse direction. This form of the chassis allows a high amount of the elastic leg feature to be located close or at the leg edge with no or only little inclination of the elastic leg feature with respect to the transverse direction.

According to a further example embodiment of the disclosure, at least the front and/or back portion is extensively made of at least two sheets of web material that are laminated together, at least one of the sheets of web material has been folded around the leg elastic feature to form a folded edge, wherein the folded edge defines the leg edge. This design allows very close positioning of the elastic web feature to the folded leg edge while avoiding adhesive on the manufacturing equipment due to manufacturing tolerances.

According to a further example embodiment of the disclosure, the front and back portions are made of individual parts that are mutually interconnected by means of the absorbent body, and the folded edge at the leg edge is substantially parallel with the transverse direction.

According to a further example embodiment of the disclosure, the folded portion of the at least one sheet of web material that was folded around the leg elastic feature to form a folded edge has a width of at least 5 millimetres, specifically at least 10 millimetres, and more specifically at least 20 millimetres. This width of the folded edge allows a satisfactory level of stability of the assembly of web material and elastic leg feature.

According to a further example embodiment of the disclosure, the leg edge is the leg edge of the front portion of the absorbent article.

The method may, according to an example embodiment of the disclosure, further comprise forming the chassis by means of cutting away pieces of the web material, wherein part of the elastic leg feature is cut away simultaneously with cutting of the leg edge of the chassis. Simultaneous cutting of the leg edge and elastic waist feature allows the elastic leg feature to follow the contour of the leg edge without accurate positioning of the elastic leg feature during the manufacturing process.

The method may also alternatively, according to a further example embodiment of the disclosure, comprise forming the chassis by means of:

feeding a first continuous sheet of web material in a machine-direction;

fastening the leg elastic feature in a tensioned state to a first continuous sheet of web material, wherein the leg elastic feature is located offset from a crotch-side edge of the first sheet, such that a strip of material of the first sheet remains between a crotch-side edge of the leg elastic feature and the crotch-side edge of the first sheet;

folding the strip of material of the first sheet around the leg elastic feature to form a folded edge, wherein the elastic leg feature is located at the folded edge;

feeding a second continuous sheet of web material parallel with the first continuous sheet of web material, such that the first and second continuous sheets of web material are located side by side and offset from each other in a machine cross-direction; and mutually interconnecting the first and second sheets of web material by means of an absorbent body.

Folding of the edge of a sheet of web material around the elastic leg feature allows the elastic leg feature to become positioned very close to the folded leg edge without accurate positioning of the elastic leg feature during the manufacturing process and with reduced risk for adhesive contamination of the manufacturing equipment.

The array of gender-specific, disposable absorbent articles may according to an example embodiment of the disclosure be further defined in that each first disposable absorbent article has a first elastic leg feature and a first elastic waist feature, and in that each second disposable absorbent article has a second elastic leg feature and a second elastic waist feature, wherein the width of the first elastic leg feature is smaller than the width of the second elastic leg feature, and wherein the width of the first elastic waist feature is smaller than the width of the second elastic waist feature. This array of gender-specific disposable absorbent articles enables even more adaptation of the absorbent article to the specific anatomy of each gender, such that the pant-type absorbent article may benefit from increased comfort and fit.

Further areas of applicability will become apparent from the description provided herein.

BRIEF DESCRIPTION OF DRAWINGS

In the detailed description below reference is made to the following figure, in which:

FIG. 6a shows a schematic illustration of a pant-type absorbent article in a flat state, FIG. 6b shows a magnification of a view of FIG. 6a, FIG. 7 shows a schematic illustration of a pant-type absorbent article having an alternative chassis-shape, FIG. 8 shows a similar view as FIG. 6a but with more details concerning elastic features, FIG. 15 shows a schematic illustration of yet a further alternative pant-type absorbent article in a flat state, FIG. 16a shows a first manufacturing step of the article of FIG. 15, FIG. 16b shows a second manufacturing step of the article of FIG. 15, FIG. 16c shows a cross-sectional cut A-A of FIG. 15, FIG. 17 shows an alternative cross-sectional cut, FIG. 18 shows still an alternative cross-sectional cut.

DETAILED DESCRIPTION OF EXAMPLE EMBODIMENTS

Various aspects of the disclosure will hereinafter be described in conjunction with the appended drawings to illustrate and not to limit the disclosure, wherein like designations denote like elements, and variations of the described aspects are not restricted to the specifically shown embodiments, but are applicable on other variations of the disclosure.

Figure 1:
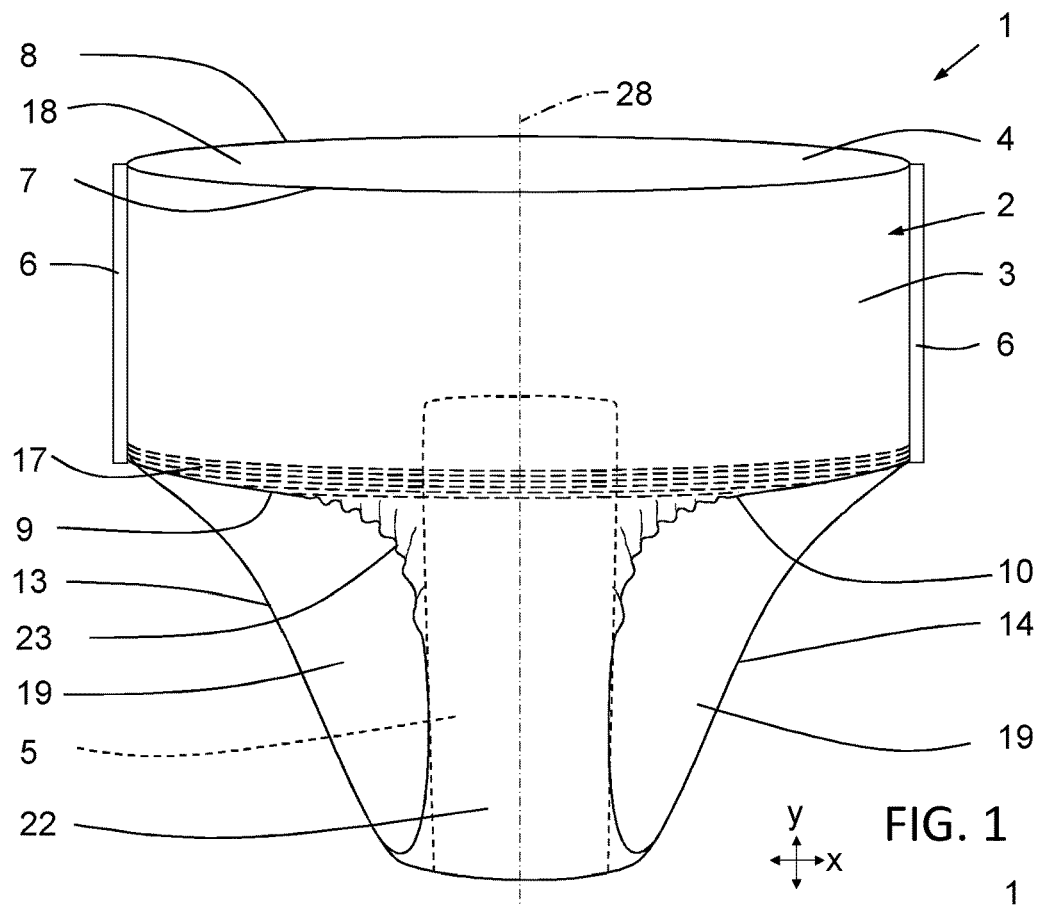
FIG. 1 shows a schematic illustration of a perspective front view of a pant-type article according to the disclosure.

In FIG. 1 of the drawings an example embodiment of a disposable pant-type absorbent article 1 is schematically illustrated in an assembled and ready-to-use state. The pant-type absorbent article 1 is for example pant diaper, a sanitary pant or an incontinence pant adapted for use by a baby, child or adult, male or female user. The pant-type absorbent article 1 according to the example embodiment of FIG. 1 comprises a single-piece chassis 2 having a front portion 3, a back portion 4, a crotch portion 22 connecting the front and back portions 3, 4, and a centre line 28 in the longitudinal direction of the article. The front portion 3 further has a waist edge 7, a pair of leg edges 9, 10 and a pair of side edges 11, 12. The back portion 4 further has a waist edge 8, a pair of leg edges 13, 14 and a pair of side edges 15, 16. The absorbent article 1 further comprises an absorbent body 5 located mainly in the crotch portion 22 of the article 1. The absorbent body 5 may be manufactured separately from the chassis 2 and inserted and fastened to the chassis 2 at a suitable manufacturing step. Side edges of the front portion 3 are attached to opposite side edges of the back portion by means of permanent or re-closable side connections 6, such as side seams, hook and loop fasteners, adhesive fasteners, or the like, such as to at least partly define a waist-opening 18 and a pair of leg-openings 19.

An elastic leg feature 17 is fastened to the chassis 2 at least partly along the leg edges 9, 10 of the front portion 2 for the purpose of providing the absorbent article with a good fitting to the legs of the user wearing the article. The elastic leg feature 17 is fastened close to the leg edges 9, 10 for substantially eliminating creation of frills 23 along the leg edges 9, 10. Frills 23 herein refers to gathered fabric at an edge of the web material of the chassis. Frills 23 typically occur at a leg edge when the leg edge is located sufficiently offset from an elasticised surface area of a web material. When the offset is large the non-elasticised web material of the edge will contract and gather in large undulations along the leg edge, thereby forming frills 23. However, when an elastic leg feature 17 is fastened to the web material at a location closer to the leg edge, less non-elasticised web material is available at the leg edge 9, 10, such that less frills 23 is created.

Large frills 23 at the leg edge 9, 10 may be sensed as uncomfortable by a user and perceived by a user as rendering the absorbent article 1 less secure against leakage. Having the elastic leg feature 17 positioned closer to the leg edge 9, 10 may also results in an absorbent article 1 having an improved fit to the shape of the legs of the user. It is thus desirable to provide an elasticised leg edge 9, 10 of the front and/or back portion 3, 4 that has a more cuff like appearance with less frills 23, thereby providing the absorbent article 1 with an appearance more similar to cloth underwear.

Fastening of elastic leg feature 17 close to an edge of a web material, such as closed to the leg edge 9, 10, 13, 14 of the chassis 2, is difficult due to the manufacturing tolerances of the production line. The manufacturing line for the pant-type absorbent article normally operates at a very high rate and the fully automatized manufacturing line tends to have a certain amount of tolerances.

Figure 3:
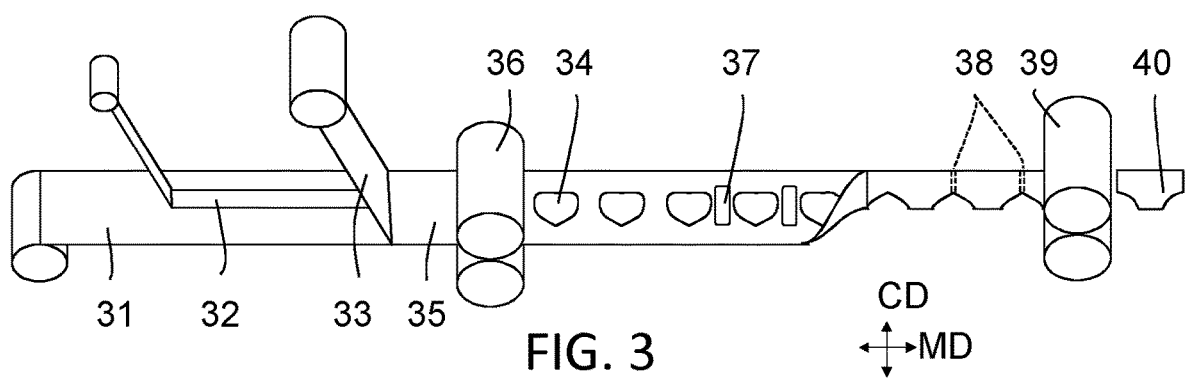
FIG. 3 shows a schematic illustration of a first manufacturing process for a pant-type absorbent article.

An example embodiment of a manufacturing line for a pant-type absorbent article having cut-out leg openings is schematically illustrated in FIG. 3. A first continuous sheet 31 of web material is supplied and a strip 32 of elastic material is attached to the first sheet 31 in a tensioned state. The strip 32 of elastic material may be glued or otherwise fastened to the first continuous sheet 31 of web material, and the strip 32 is intended to form an elastic web feature of the absorbent article 1. Thereafter a second continuous sheet 33 of web material is joined to the first sheet to form a laminated product having the strip 32 of elastic material sandwiched between the first and second sheets 31, 33. The first and second sheets 31, 33 may be attached to other by ultrasonic bonding, welding, adhesive, embossing, mechanical fastening, or the like. The attachment of the first sheet 31, strip 32 and second sheet 33 is here described as being performed in consecutive steps but these steps are typically performed in a single step.

In a subsequent step leg openings 34 are cut out of the laminated web material 35 forming the chassis of finished absorbent articles. The cutting may be performed by any type of suitable cutting equipment 36, such as rolling cutting using two opposite rollers. Thereafter an absorbent body 37 may be attached to the chassis using any known fastening technology, such as ultrasonic bonding, welding, adhesive, embossing, mechanical fastening, or the like. After mounting of the absorbent body 37 the continuous first and second sheets 31, 33 are folded, such that the first sheet 31 becomes an outer sheet of the chassis and the second sheet becomes inner sheet of the chassis, and with the absorbent body 37 located inside of the second sheet 33. After for example welding of side seams 38 the continuous assembly of inner and outer sheets 31, 33 and absorbent body are cut into individual absorbent articles 40 by means of cutting equipment 39.

A similar process for manufacturing an absorbent article with a H-chassis will be briefly described with reference to FIG. 4. A first continuous sheet 41 of web material is supplied and a strip 43 of elastic material is attached to the first sheet 41 in a tensioned state. The strip 43 of elastic material may be glued or otherwise fastened to the first continuous sheet 31 of web material, and the strip 43 is intended to form elastic web feature of the absorbent article 1. Thereafter a second continuous sheet 44 of web material is joined to the first sheet 41 to form a laminated product having the strip 43 of elastic material sandwiched between the first and second sheets 41,44. The first and second sheets 41, 44 may be attached to other by ultrasonic bonding, welding, adhesive, embossing, mechanical fastening, or the like. The width of the second sheet 44 may be slightly smaller than the width of the first sheet 41, such that strip 45 of material having a single layer is formed at the edge of the first sheet 41 intended to form the leg edge of the absorbent article. This strip 45 is subsequently folded onto the outer surface of the second sheet 44, such that the strip 43 of elastic material becomes located at the fold line 46. A continuous sheet 42 of web material are supplied parallel to and offset from the first and second sheets 41, 44, wherein the laminate of the first and second sheets 41, 44 is arranged to form the front portion of the chassis and the third sheet 42 is arranged to form the back portion of the chassis. Thereafter absorbent bodies 47 are attached to the chassis using any known fastening technology, such as ultrasonic bonding, welding, adhesive, embossing, mechanical fastening, or the like. The absorbent bodies 47 connect the laminate of the first and second sheets 41, 44 with the third sheet 42. After mounting of the absorbent body 47 the chassis is folded, such that the absorbent body 47 becomes located inside of the chassis. After for example welding of side seams the chassis the assembly is cut into individual absorbent articles 48 by means of cutting equipment 49.

It is clear from the above description of the these two example manufacturing processes that a relative position between a moveable supply of web material and fixed equipment of the manufacturing line may vary over time to a certain extent. As a result, the final position of any fastened elastic leg feature on the final absorbent article may vary slightly between individual absorbent article items, and cutting operations of a continuous supply of web material will involve a certain amount of variation in the relative position of the cutting and the moveable web material.

Due to these manufacturing tolerances the manufacturing line may be arranged to fasten the elastic leg feature slightly offset from the intended leg edge for avoiding that the elastic leg feature is cut or damaged during a subsequent cutting step, or that the elastic leg feature is mounted partly outside of the surface of the web material. Unintended cutting or damaging of the elastic leg feature may impair the functionality of the elastic leg feature, and mounting of the elastic leg feature outside the surface of the web material may result in that adhesive of the elastic leg feature comes into contact with the manufacturing line, such that manufacturing line must be halted and cleaned.

It is thus desirable to have the elastic leg feature mounted as close as possible to the leg edge of the chassis for improved comfort, fit and deemed leakage protection while handling the manufacturing tolerances, risk for unintended damages to the elastic leg feature during cutting, risk of having adhesive applied to the manufacturing equipment, etc.

This disclosure provides two different approaches for accomplishing improved comfort, fit and leakage protection while handling the manufacturing tolerances. According to a first approach, as will be described with reference to FIGS. 1-3 and 5-14, an elastic leg feature is first mounted on a web material intended for forming the front and/or back portion of the chassis. In a subsequently step the web material is cut in a cutting step for forming at least the leg opening of the absorbent article. According to the first approach, the desired relative position between the web material and a cutting tool is selected such a part of the elastic leg feature attached to the web material is intended to be cut-away during the cutting step. By having the elastic leg feature designed from the beginning for being partly cut away during the manufacturing process the remaining elastic effect of the elastic leg feature after cutting will not be impaired beyond an acceptable level. Hence, the controlled removal of a portion of the elastic leg feature, taking into account the manufacturing tolerances of the production line, ensures that sufficient elasticity performance is still available after cutting of the elastic leg feature. As a result, the leg edge of the chassis will, at least at the location where the elastic leg feature was cut together with cutting the leg edge, have an elastic leg feature 17 fastened very close to the leg edge, such that a leg edge with cuff like appearance without frills is provided.

According to a second approach for accomplishing improved comfort, fit and leakage protection while handling the manufacturing tolerances, an absorbent article with a H-chassis configuration is provided, as will be described with reference to FIGS. 4 and 15-17. Here, an elastic leg feature is first mounted offset from an edge of a web material intended for forming the front or back portion of the chassis. The level of offset is selected in view of the manufacturing tolerance to ensure that the elastic leg feature is substantially always attached entirely on the web material for avoiding adhesive on the manufacturing equipment. In a subsequent step the web material carrying the elastic web feature is folded along the edge of the elastic leg feature, such that the elastic leg feature becomes located directly at the leg edge of the front or back portion. As a result, also this approach provides elastic leg feature 17 fastened very close to the leg edge while taking onto account manufacturing tolerance, such that a leg edge with cuff like appearance without frills is provided.

Figure 2:
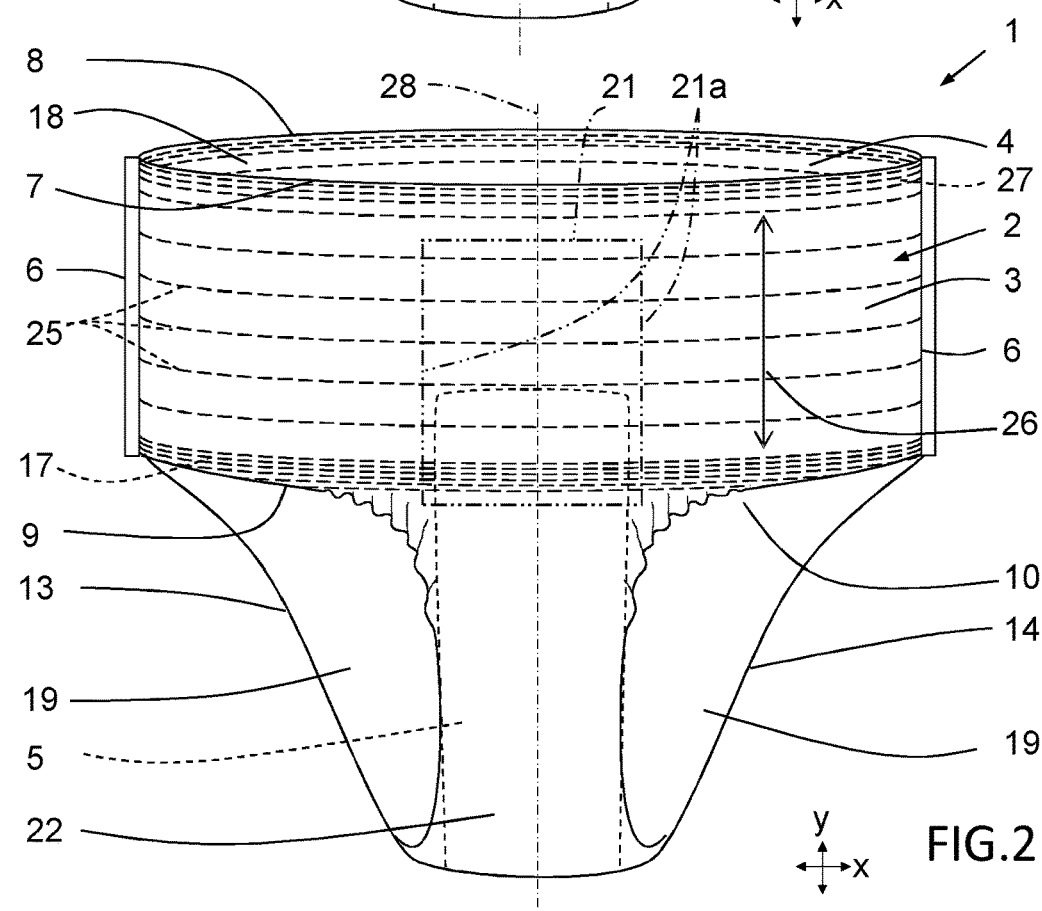
FIG. 2 shows a similar view as FIG. 1 but with more details concerning elastic features.

The pant-type absorbent article 1 schematically illustrated in FIG. 1 corresponds to a basic version of an absorbent article, and generally pant-type absorbent articles include more elastic features for enabling a user to put on an absorbent article without having the side the permanent or re-closable side connections, such as side seams, damaged due to overstress. For example, an absorbent article 1 corresponding to the absorbent article of FIG. 1 but with more elastic features is schematically illustrated in FIG. 2. This absorbent article 1 has front and back portions 3, 4 that are extensively made of an elastic web material, wherein the elastic web material may be made of at least two substantially inelastic sheets of web material that are laminated together and having an elastic feature 25 sandwiched between said at least two sheets of web material, and wherein the elastic feature is attached to the at least two sheets in a tensioned state in the transverse direction x to provide a web material that is elasticized in the transverse direction x. The elastic feature 25 may for example comprise a plurality of elastic threads extending in the transverse direction x and placed offset from each other. This elastic feature may for example form an elastic centre region 26.

An elastic waist feature 27 may be additionally fastened to the chassis 2 along the waist edge 7, 8 of the front and back portions 3, 4. The elastic waist feature 27 of the front and back portions preferably extends in a transverse direction x substantially parallel with each waist edge 7, 8. The elastic waist feature 27 and/or the elastic leg feature 17 typically have a stronger elasticity than the elastic feature of the centre region 26.

FIG. 6a illustrates schematically a pant-type absorbent article 1 in a flat state and with the permanent or re-closable side connections 6 in a non-connected state. The pant-type absorbent article 1 is of the type having cut-out leg openings 19, and where the elastic leg feature 17 has been partly cut-away during cutting of the leg openings 19.

For accomplishing a satisfactory level of comfort, fit and leakage protection the elastic leg feature 17 is arranged to extend from the associated side edge 11, 12 towards a centre line 28 in the longitudinal direction y of the article 1. Thereby a proper length of the desired leg cuff along the leg edge 9, 10 is enabled. This is also a result if the production method disclosed with reference to FIG. 3 is used.

Furthermore, as illustrated in FIG. 6a in connection with the magnification of area 61 in FIG. 6b, when a portion of the leg elastic feature 17 having a first length L1, in which a distance D between any point of each leg edge to the nearest part of the elastic leg feature, in a longitudinal direction, is less than for example 6 millimetres, and when the first length L1 is at least 55% of a maximal length L2 of the leg opening in the transverse direction x, as measured in an extended state of the absorbent article, a satisfactory length of a proper leg cuff along the leg edge 9, 10 is available for providing a satisfactory level of comfort, fit and leakage protection.

The distance D between any point of each leg edge 9, 10 to the nearest part of the elastic leg feature 17, in a longitudinal direction y, is here used for indicating the quality of the leg cuff in terms of existence of frills or frill size. As described above, having the elastic leg feature 17 located close the leg edge 9, 10 means that the chassis material of the front portion 3 does not show any frills, or at least only small frills, since only web material having no elastic feature can develop large frills. The nearest part of the elastic leg feature 17 may be represented by the nearest elastic thread in case the elastic leg feature comprises a plurality of elastic threads. In case the distance D is selected as being less than 5 millimetres or even less than 4 millimetres, the quality level of the leg cuff may be deemed as being even better.

The first length L1, as measured in the transverse direction x, is here used as an indication of the length the high quality leg cuff, and the first length L1 is compared with the maximal length L2 of the leg opening in the transverse direction x for providing a sensible way for determining the first length L1 independent from size of the specific absorbent article. The maximal length L2 of the leg opening in the transverse direction x may be easily and unambiguously determined by measuring the maximal length, in the transverse direction x, between an extension 60 running from a transverse outermost portion of the side edge 11, 12 of the front portion 3 to a transverse outermost portion of the side edge 15, 16 of the back portion 4, as schematically illustrated in FIG. 8, which shows an absorbent article having inclines side edges 11, 12, 15, 16 with respect to the longitudinal direction y. The transverse direction x in perpendicular to the longitudinal direction y.

Preferably, the first length should be at least 55% of a maximal length L2 of the leg opening in the transverse direction x, as measured in an extended state of the absorbent article. 55% is deemed representing a value that gives satisfactory result with respect to increased comfort and fit and that providing the user with confidence with respect to its leakage protection.

Figure 9:
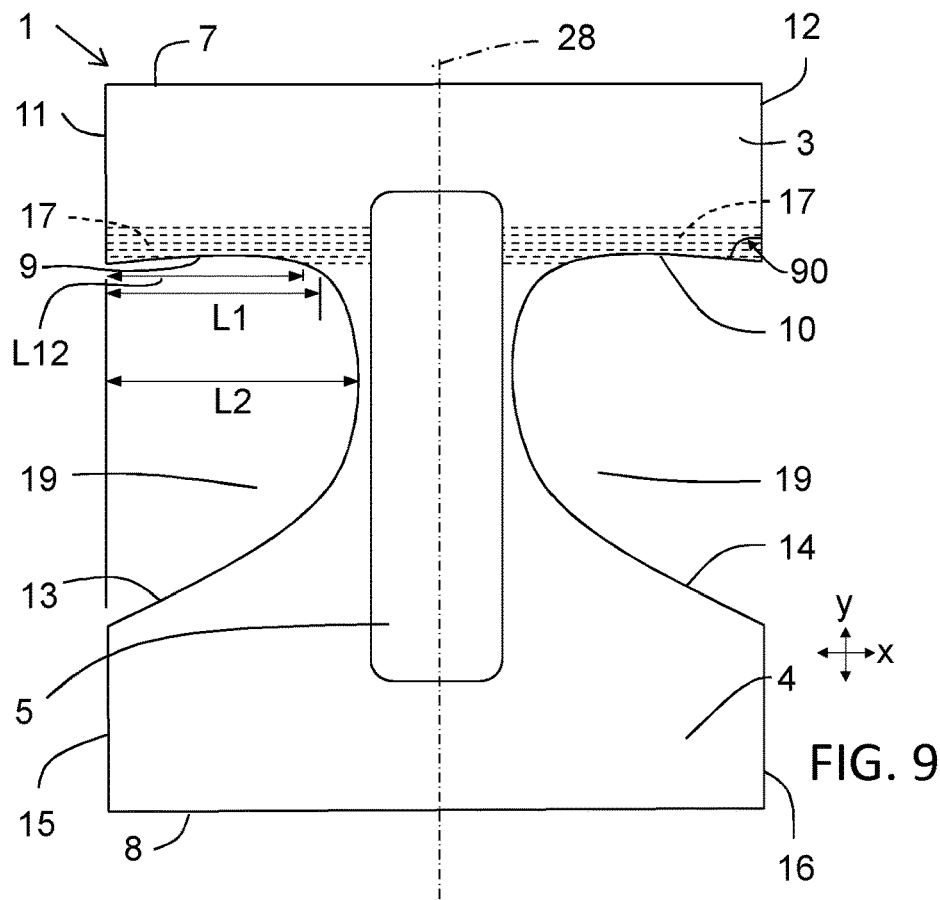
FIG. 9 shows a schematic illustration of an alternative pant-type absorbent article in a flat state.

An alternative approach for defining the desired length of the leg elastic feature 17 is to define a second length L12 as the maximal length in the transverse direction x from the side edge 11, 12, 15, 16 to a point along the periphery of the leg edge 9, 10 having a cut leg elastic feature 17, wherein the second length L12 should be at least 30%, specifically at least 40%, and more specifically at least 50% of a maximal length L2 of the leg opening 19 in the transverse direction x, as measured in an extended state of the absorbent article. This alternative definition is also deemed to result in a absorbent article having the desired characteristics of increased comfort and fit and that providing the user with confidence with respect to its leakage protection. The second length L12 is illustrated in FIGS. 6a, 9 and 15 but is applicable to all example embodiments of the present disclosure.

The term "extended state" of the absorbent article is herein defined as a state in which the absorbent article has been extended in all four direction to such an extent that all the elastic materials contained therein, such as the elastic web material, the waist elastics, the leg elastics, are extended to such an extent that they will not gather any part of the product, but the entire absorbent article is completely flat and in an un-gathered state. The article is extended only to such an extent that this flat condition is reached.

The first length L1 may additionally be defined in terms of an absolute length. For example, the absorbent article may be configured to have a first length L1 of at least 5 centimetres, specifically at least 10 centimetres, and more specifically at least 15 centimetres in the transverse direction, starting from the side edge 11, 12 of the front or back panel where the elastic leg feature is fastened, as measured in an extended state of the absorbent article 1.

The elastic leg feature may according to an example embodiment comprise a set of 3 to 10 individual elastic threads, specifically 4 to 8 individual elastic threads, or more specifically 5 to 7 individual elastic threads. In the illustration of FIG. 6a six elastic threads are included. In the illustration of FIG. 6a all six individual elastic threads are placed parallel to each other and with a gap 63 of about 3 millimetres between neighbouring threads, as measured in an extended state of the absorbent article. However, the gap may be anywhere in the range of 1 to 6 millimetres, depending on for example thread material, thread dimension, thread strength, level of thread pretension used, etc.

Similarly, depending on parameters such as number of threads used, thread material, thread dimension, thread strength, level of thread pretension used, and of course the gap 63 between neighbouring threads, a distance 64 between the outermost individual elastic threads of the elastic leg feature in a width direction of the elastic leg feature 17 may be from 3 to 60 millimetres, specifically 8 to 40 millimetres, and more specifically 15 to 28 millimetres, as measured in an extended state of the absorbent article. The width direction of the elastic leg feature 17 herein refers to a direction perpendicular to the longitudinal direction of the elastic leg feature 17.

As a consequence of the cutting of the elastic leg feature 17 at least one individual elastic thread of the elastic leg feature 17 will be substantially shorter than another individual elastic thread of said elastic leg feature 17. For example, at least one individual elastic thread of the elastic leg feature 17 may be at least 3 centimetres, specifically at least 5 centimetres, and more specifically at least 7 centimetres shorter than another individual elastic thread of said elastic leg feature 17, as measured in an extended state of the absorbent article. For the same reason, the number of individual elastic threads of the elastic leg feature 17 will tend to vary along the length of the elastic leg feature 17.

The elastic leg feature 17 may of course alternatively be formed of an elastic band, which has a certain width and a certain thickness. The width of the band in a width direction of the elastic leg feature 17 may for example be from 3 to 60 millimetres, specifically 8 to 40 millimetres, and more specifically 15 to 28 millimetres, as measured in an extended state of the absorbent article. At least part of the elastic band configured to be cut off during cutting of the leg edge 9, 10 of the front portion 3 of the chassis 2 for the purpose of providing a long first length L1 having a proper leg cuff along the leg edge 9, 10. The width of the band may thus vary along a longitudinal direction of the band considering that it is configured to be cut at least partly along the leg edge 9, 10.

In the specific illustration of FIG. 6a a length 65 of the leg edge 9, 10 of the front portion 3 in the longitudinal direction y is significantly less than a length 66 of the leg edge 9, 10 of the front portion 3 in the transverse direction x. This design of the leg edge of the front portion 3 enables use of an elastic leg feature 17 that is more parallel with the transverse direction x without requiring a relatively large width of the elastic leg feature for compensating relatively large cut-off in one side of the elastic leg feature 17. The length 65 of the leg edge 9, 10 of the front portion 3 in the longitudinal direction y may for example be less than 50% of the length 66 of the leg edge 9, 10 of the front portion 3 in the transverse direction, specifically less than 35%, and more specifically less than 20%. However, the disclosed cutting shape of the leg openings 19 illustrated in FIG. 6a is merely an example and many variations are possible within the scope of the disclosure.

The pant-type absorbent article 1 schematically illustrated in a flat state in FIG. 6a corresponds to a basic version of an absorbent article, and pant-type absorbent articles generally include more elastic features for reducing the risk for damages on the side connections 6 when a user puts on the absorbent article, as well as for improving comfort, fit and leakage protection. For example, an absorbent article 1 corresponding to the absorbent article of FIG. 6a but with more elastic features is schematically illustrated in FIG. 8. This absorbent article 1 has at least a front portion 3 made extensively of an elastic web material that is elasticized in the transverse direction x. The elastic feature 25 in the centre region 26 may for example comprise a plurality of elastic threads extending in the transverse direction x and placed offset from each other.

An elastic waist feature 27 may be additionally fastened to the chassis 2 along the waist edge 7 of at least the front portion 3. The elastic waist feature 27 of the front portion preferably extends in a transverse direction x substantially parallel with the waist edge 7. The elastic waist feature 27 and/or the elastic leg feature 17 typically have a stronger elasticity than the elastic feature 25 of the centre region 26. An elastic waist feature 29 may also be fastened to the chassis 2 along the waist edge 8 of at least the back portion 4. The elastic waist feature 29 of the back portion preferably extends in a transverse direction x substantially parallel with the waist edge 8.

An elastic leg feature 80 is also disclosed extending substantially in the longitudinal direction in at least the crotch portion 22 of the absorbent article 1. The elastic leg feature 80 of the crotch portion may be an individual elastic feature different from the elastic leg feature of the leg edge of the front and back portions 3, 4. The elastic leg feature 80 of the crotch portion 22 may comprise one or more, for example two, three, or four individual elastic threads that are arranged substantially parallel with each other and offset from each other in the transverse direction x. Alternatively, the elastic leg feature 80 in the crotch portion 22 may comprises a band of elastic material. The elastic leg feature 80 in the crotch portion 22 us shown being fastened to the chassis 2 but it may be advantageous in a manufacturing point of view to instead provide the elastic leg feature 80 of the crotch portion 22 on the absorbent body 5 instead.

The absorbent article of FIG. 8 further discloses an elastic leg feature 20 on the back portion 4. The elastic leg feature 20 on the back portion 4 may extend substantially in the transverse direction x. The elastic leg feature 20 on the back portion 4 may further comprise one or more individual elastic threads, such as for example 2 to 8 threads.

The approach of cutting the part of the elastic leg feature 17 disclosed in relation to the front portion 3 of the absorbent article 1 may also be performed on the elastic leg feature 20 of the back portion 4.

During cutting of the web material in the cutting equipment 36 in the manufacturing process described with reference to FIG. 3, it may be advantageous to avoid cutting of sections that are parallel with the machine direction MD. Therefore, the chassis 2 in FIG. 3 is cut such that an initial direction of orientation of the leg edge 9, 10, starting from the side edge 11, 12, deviates from the transverse direction x away from the waist edge 7, such that an obtuse angle 90 between the longitudinal direction y and the initial direction of orientation of the leg edge 9, 10 near the side edge 11, 12 is formed, as measured in an extended state of the absorbent article 1. An alternative solution for to the obtuse angle 90 is to provide the chassis with acute angle 90 instead, as illustrated in FIG. 9. Here, the chassis 2 is cut such that an initial direction of orientation of the leg edge 9, 10, starting from the side edge 11, 12, deviates from the transverse direction x towards the waist edge 7, such that an acute angle 90 between the longitudinal direction y and the initial direction of orientation of the leg edge 9, 10 near the side edge 11, 12 is formed, as measured in an extended state of the absorbent article 1. Furthermore, as a result of the acute angle 90, the smallest width of the elastic leg feature may be located offset from the side edge 11, 12 as certain amount, as shown in FIG. 9.

Figure 10:
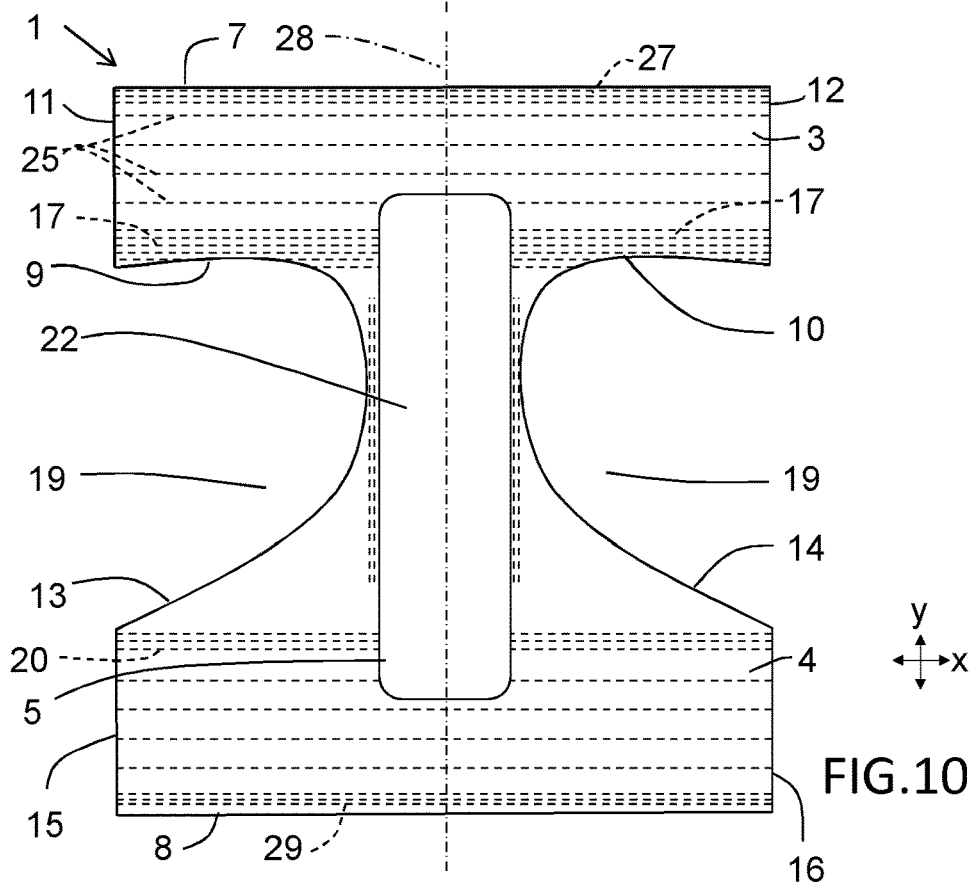
FIG. 10 shows a similar view as FIG. 9 but with more details concerning elastic features.

An example embodiment of an absorbent article 1 corresponding to the absorbent article of FIG. 9 but with more elastic features is schematically illustrated in FIG. 10. This absorbent article 1 has at least a front portion 3 made extensively of an elastic web material that is elasticized in the transverse direction x. The elastic feature 25 in the centre region may for example comprise a plurality of elastic threads extending in the transverse direction x and placed offset from each other.

An elastic waist feature 27 may be additionally fastened to the chassis 2 along the waist edge 7 of at least the front portion 3. The elastic waist feature 27 of the front portion preferably extends in a transverse direction x substantially parallel with the waist edge 7. The elastic waist feature 27 and/or the elastic leg feature 17 typically have a stronger elasticity than the elastic feature 25 of the centre region 26. An elastic waist feature 29 may also be fastened to the chassis 2 along the waist edge 8 of at least the back portion 4. The elastic waist feature 29 of the back portion preferably extends in a transverse direction x substantially parallel with the waist edge 8.

An elastic leg feature 80 is also disclosed extending substantially in the longitudinal direction in at least the crotch portion 22 of the absorbent article 1. The elastic leg feature 80 of the crotch portion may be an individual elastic feature different from the elastic leg feature of the leg edge of the front and back portions 3, 4. The elastic leg feature 80 of the crotch portion 22 may comprise one or more, for example two, three, or four individual elastic threads that are arranged substantially parallel with each other and offset from each other in the transverse direction x. Alternatively, the elastic leg feature 80 in the crotch portion 22 may comprises a band of elastic material. The elastic leg feature 80 in the crotch portion 22 is shown being fastened to the chassis 2 but it may be advantageous in a manufacturing point of view to instead provide the elastic leg feature 80 of the crotch portion 22 on the absorbent body 5 instead.

The absorbent article of FIG. 10 further discloses an elastic leg feature 20 on the back portion 4. The elastic leg feature 20 on the back portion 4 may extend substantially in the transverse direction x. The elastic leg feature 20 on the back portion 4 may further comprise one or more individual elastic threads, such as for example 2 to 8 threads.

The approach of cutting the part of the elastic leg feature 17 disclosed in relation to the front portion 3 of the absorbent article 1 may also be performed on the elastic leg feature 20 of the back portion 4. The elastic leg feature 20 of the back portion 4 is further also secured to the chassis in a non-parallel manner over the article 1.

Figure 11:
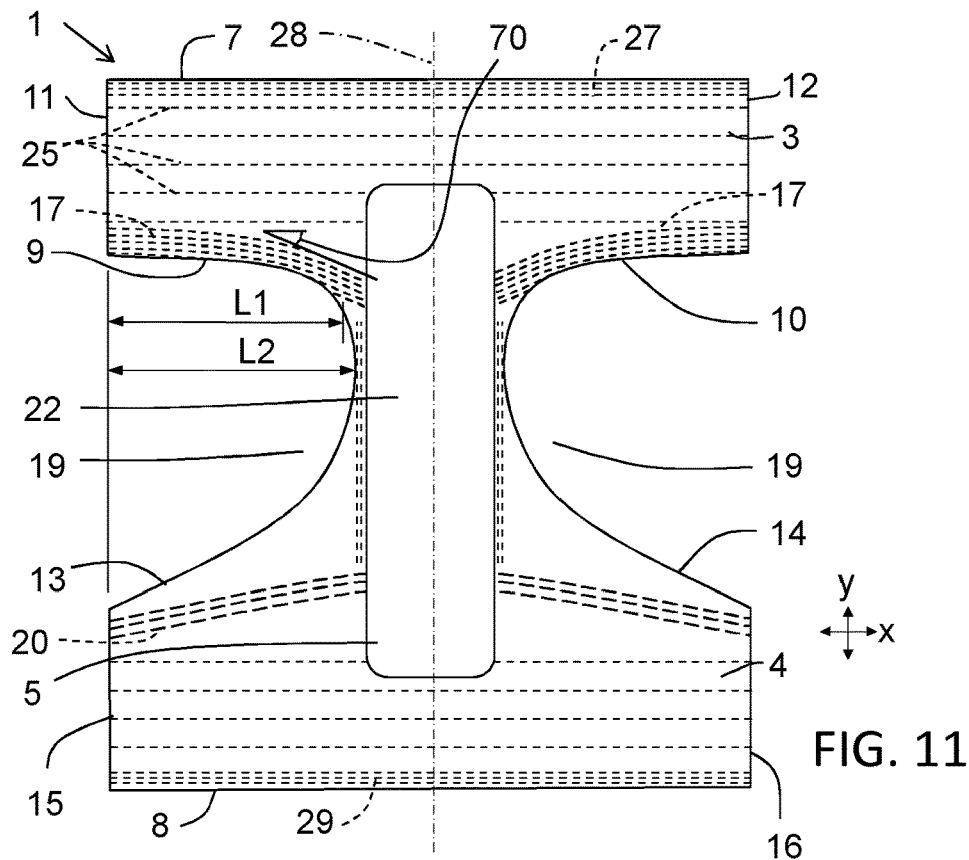
FIG. 11 shows a schematic illustration of still an alternative pant-type absorbent article in a flat state.

Still a further example embodiment of the absorbent article of the disclosure is shown in FIG. 11. This embodiment is very similar to the example embodiment shown and described with reference to FIG. 8, but with the difference that the elastic leg feature does not extend parallel with the transverse direction x over the entire width of the article in the transverse direction x. Instead, the elastic leg feature in the front portion 3 of the chassis bends along the leg edge 9, 10 a certain extent. This design corresponds to the manufacturing process shown in FIG. 5, which is a modified manufacturing process of the one shown and described with reference to FIG. 3. The manufacturing process of FIG. 5 differs from the process of FIG. 3 in that a moveable guide 32a is provided for applying the continuous strip 32 of elastic material to the first sheet 31 in a smoothly curved meander-shape while being in a tensioned state. As a result the elastic leg feature 17 in FIG. 11 follows the periphery of the leg opening 19 better and therefore renders the first length L1 to be at least 60% of the maximal length L2 of the leg opening in the transverse direction x, as measured in an extended state of the absorbent article, when D is 6 millimetres.

For enabling a high manufacturing rate the elastic leg feature 17 is arranged to have a direction of orientation deviating less than 30 degrees, specifically less than 20 degrees, and more specifically less than 10 degrees from the transverse direction x over the entire length of the elastic leg feature 17, as measured in an extended state of the absorbent article.

This arrangement enables attachment of the continuous elastic leg feature 17 to a continuous sheet of web material moving in a machine direction without significant motion of the elastic leg feature in a machine cross direction. Hence, as long as the angle 70 defined in FIG. 11 is relatively small, the manufacturing complexity increases only slightly due to operation of the moveable guide 32a. With smaller variation in inclination of the elastic leg feature with respect to the transverse direction x the elastic leg feature is still easy and fast to apply on the surface of the chassis.

Figure 12:
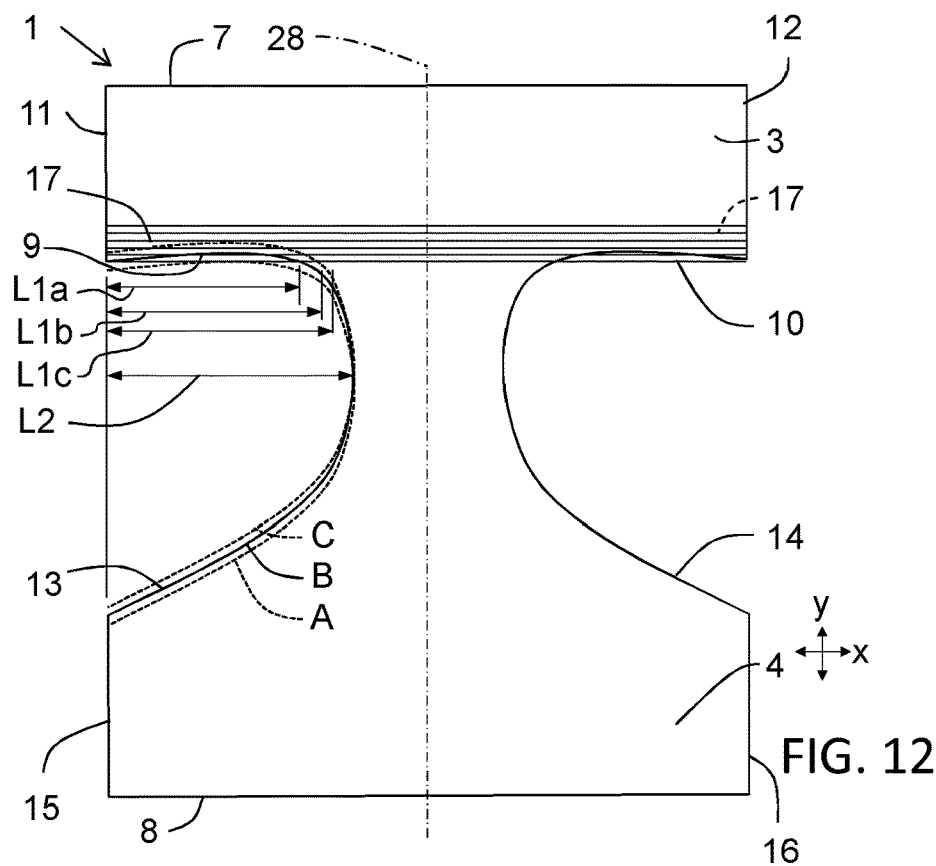
FIG. 12 shows a similar view of the effect of manufacturing tolerances.

In FIG. 12 of the disclosure the result of any manufacturing tolerances in the cross machine direction CD are shown, and how the present disclosure handles manufacturing tolerances such that a comfortable, good fitting and high leakage-protective leg cuff is provided independent of the manufacturing tolerances. Depending on the relative position in the machine cross direction CD between the web material and the location of the leg cut-out equipment the leg cut-out will be subject to variations in terms of location on the web material. Examples of these variations in cut-out position are schematically illustrated in FIG. 12 and marked as "A", "B" and "C".

For example, when the cutting equipment cuts along path "A" shown in FIG. 12, no portion of the elastic leg feature is cut away at all, and all six elastic threads remain intact and in operation. This cut location consequently results in the first length L1a and with all elastic threads intact.

Alternatively, when the cutting equipment cuts along path "B" as shown in FIG. 12, about two elastic threads appear to be cut-off and are therefore deemed missing. There remain still at least 4 elastic threads, which is sufficient for generating a first length L1b of more than 80% of the maximal length L2.

Still more alternatively, when the cutting equipment cuts along path "C" as shown in FIG. 12, three elastic threads appear to be cut-off and are therefore deemed missing. There remain still at least 3 elastic threads, which is sufficient for generating a first length L1c of more than 90% of the maximal length L2.

Figure 13:
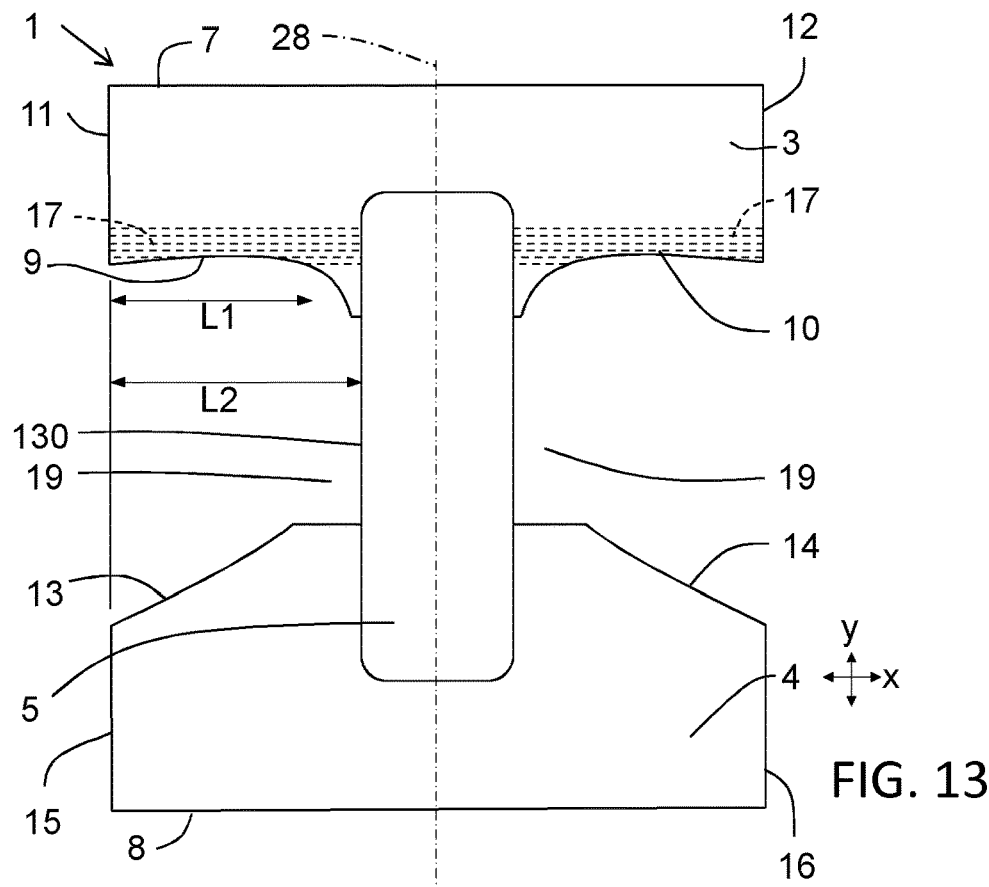
FIG. 13 shows a schematic illustration of yet an alternative pant-type absorbent article in a flat state.
Figure 14:
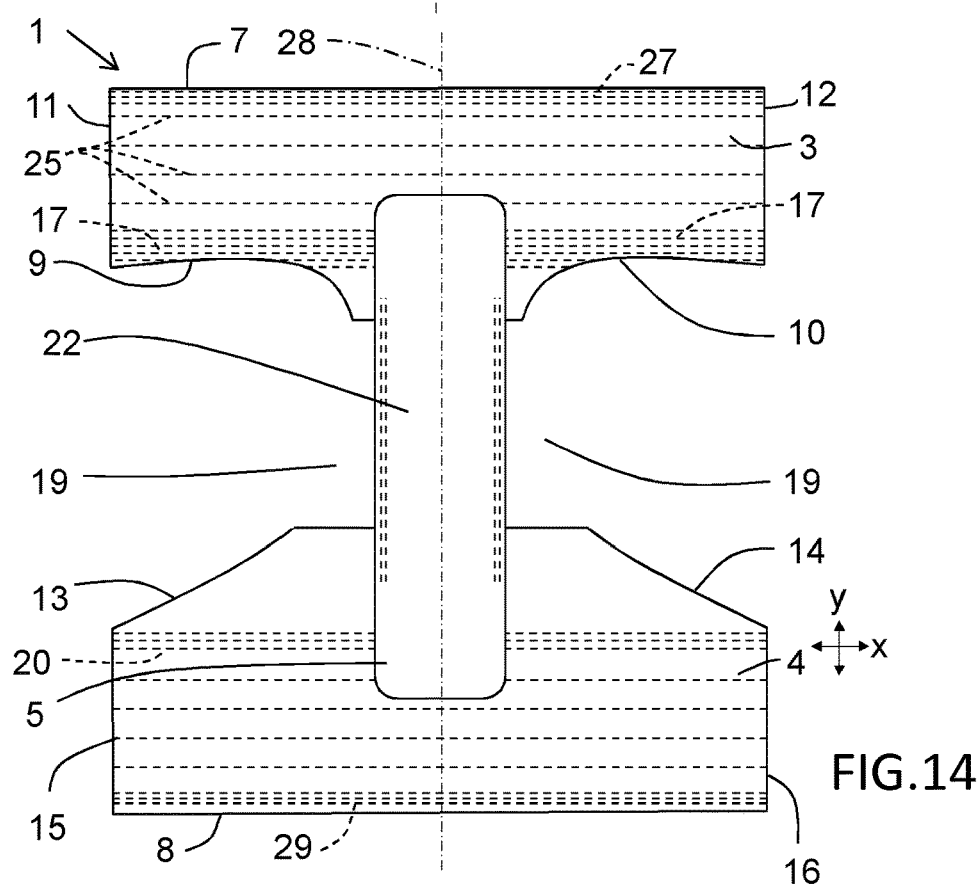
FIG. 14 shows a similar view as FIG. 13 but with more details concerning elastic features.

In the example embodiments of the absorbent article shown in FIGS. 6a to 11 the chassis was a single-piece chassis that can be manufactured according to the manufacturing process described with reference to FIG. 3. Single-piece chassis herein means a chassis having a front portion 3, a back portion 4, a crotch portion 22 connecting the front and back portions 3, 4, wherein the crotch portion 22 is made in one-piece with the front and back portions 3, 4. However, the present disclosure is not limited to single piece chassis but may equally applicable to H-chassis design, as schematically illustrated in FIG. 13 and FIG. 14. In a H-chassis design the front and back portions 3, 4 of the chassis are individual parts of the absorbent article 1, which individual parts are mutually connected by a separate absorbent body 5. In a H-chassis design the maximal length L2 of the leg opening in the transverse direction x may be partly defined by a side edge 130 of the absorbent body 5.

An example embodiment of an absorbent article 1 corresponding to the absorbent article of FIG. 13 but with more elastic features is schematically illustrated in FIG. 14. This absorbent article 1 has at least a front portion 3 made extensively of an elastic web material that is elasticized in the transverse direction x. The elastic feature 25 in the centre region may for example comprise a plurality of elastic threads extending in the transverse direction x and placed offset from each other.

An elastic waist feature 27 may be additionally fastened to the chassis 2 along the waist edge 7 of at least the front portion 3. The elastic waist feature 27 of the front portion preferably extends in a transverse direction x substantially parallel with the waist edge 7. The elastic waist feature 27 and/or the elastic leg feature 17 typically have a stronger elasticity than the elastic feature 25 of the centre region 26. An elastic waist feature 29 may also be fastened to the chassis 2 along the waist edge 8 of at least the back portion 4. The elastic waist feature 29 of the back portion preferably extends in a transverse direction x substantially parallel with the waist edge 8.

An elastic leg feature 80 is also disclosed extending substantially in the longitudinal direction in at least the crotch portion 22 of the absorbent article 1. The elastic leg feature 80 of the crotch portion may be an individual elastic feature different from the elastic leg feature of the leg edge of the front and back portions 3, 4. The elastic leg feature 80 of the crotch portion 22 may comprise one or more, for example two, three, or four individual elastic threads that are arranged substantially parallel with each other and offset from each other in the transverse direction x. Alternatively, the elastic leg feature 80 in the crotch portion 22 may comprises a band of elastic material.

The elastic leg feature 80 in the crotch portion 22 is shown being fastened to the absorbent body 5 in the lack of any chassis in the crotch region.

The absorbent article of FIG. 14 further discloses an elastic leg feature 20 on the back portion 4. The elastic leg feature 20 on the back portion 4 may extend substantially in the transverse direction x. The elastic leg feature 20 on the back portion 4 may further comprise one or more individual elastic threads, such as for example 2 to 8 threads.

The approach of cutting the part of the elastic leg feature 17 disclosed in relation to the front portion 3 of the absorbent article 1 may also be performed on the elastic leg feature 20 of the back portion 4. The elastic leg feature 20 of the back portion 4 is further also secured to the chassis in a non-parallel manner over the article 1.

Still a further example embodiment of an absorbent article 1 according to the disclosure is shown in FIG. 15, in which an absorbent article having a H-chassis is shown. An example embodiment of a corresponding cross-section along cut A-A is shown in FIG. 16c. The absorbent article 1 comprises a front portion 3, and back portion 4 and a separate absorbent body 5 located in a crotch portion for connecting the front and back portions 3, 4. The front portion 3 may for example be made of two sheets 71, 72 of web material that are laminated together, wherein a first sheet 71 of web material has been folded around the leg elastic feature 17 to form a folded edge 73, wherein the folded edge 73 defines the leg edge 9, 10 of the front portion 3. An example embodiment of a manufacturing sequence of the front portion is schematically illustrated in FIG. 16a-16c. In FIG. 16a an elastic leg feature 17 has been attached to the first sheet 71 of web material, for example by means of adhesive. The elastic leg feature 17 is attached offset from an edge 75 of the first sheet 71 for reducing the risk that the elastic leg feature 17 is attached beside the first sheet 71 due to manufacturing tolerances, because this would possibly result in adhesive becoming located on the underlying manufacturing equipment, such as transport band, etc., and this is undesirable.

In a subsequent step, as shown in FIG. 16b, a portion of the first sheet 71, herein referred to as folded portion 74, has been folded around the leg elastic feature 17 to form the folded edge 73. The folded portion 74 of the first sheet 71 has width 76 of at least 5 millimetres, specifically at least 10 millimetres, and more specifically at least 20 millimetres.

The folded portion 74 may have sufficient width 76 to completely cover the leg elastic feature 17, i.e. a width sufficient for completely embedding the leg elastic feature 17 between the first sheet 71 and the folded portion 74 of the first sheet 71.

Subsequently, in FIG. 16c, the second sheet 72 is laminated to the assembly of the first sheet 71 and the elastic leg feature 17. As a result, the elastic leg feature 17 is located substantially at the folded edge 73, which forms the leg edge 10 of the front portion. This design thus cost-effectively reduces the amount of frills along the leg edge 9, 10, 13, 14 and creates a cuff-like appearance and comfort of the absorbent article 1.

Figure 4:
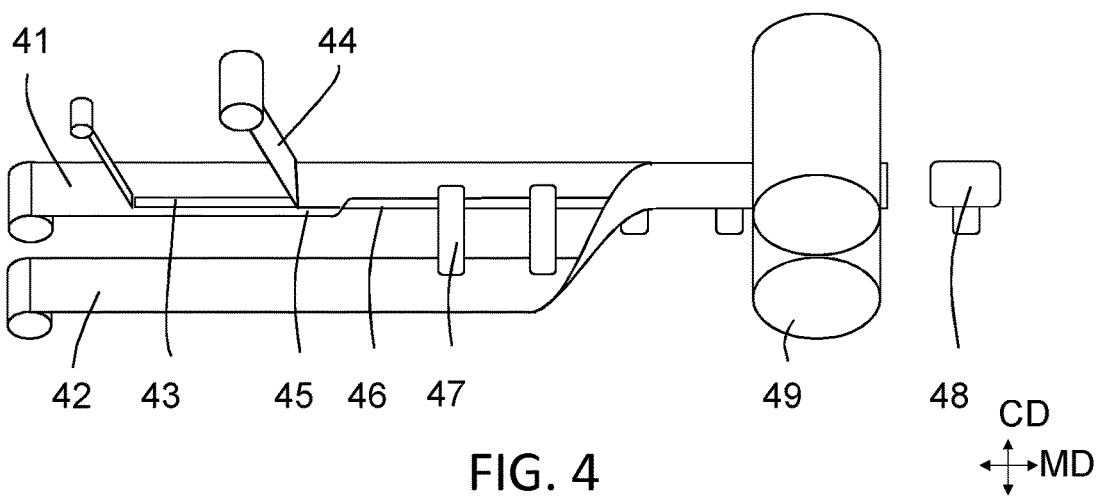
FIG. 4 shows a schematic illustration of a second manufacturing process for a pant-type absorbent article.
Figure 5:
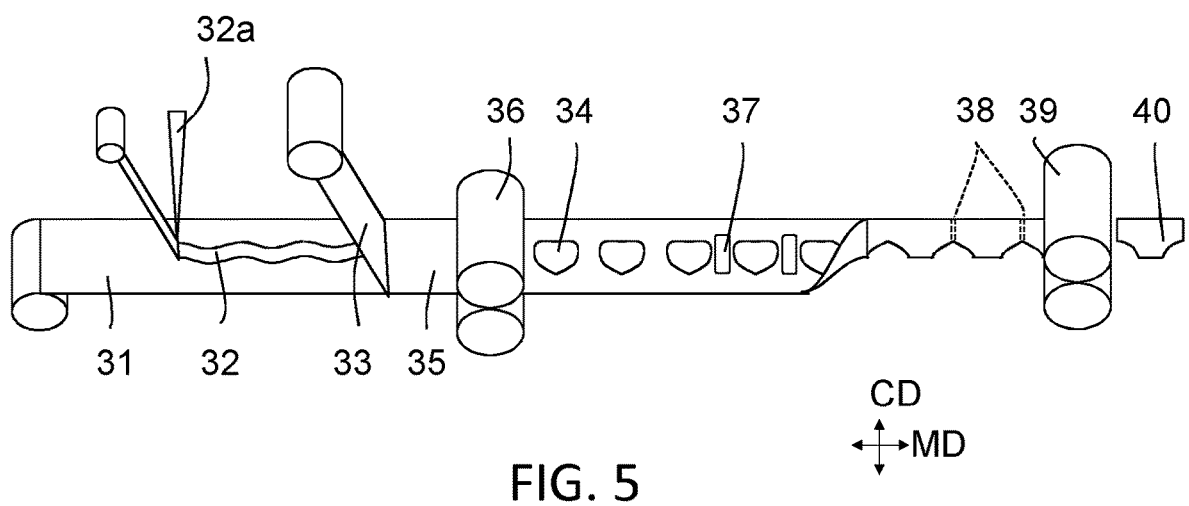
FIG. 5 shows a schematic illustration of a variation of the first manufacturing process.

The manufacturing sequence shown in FIG. 16a-16c corresponds substantially to the manufacturing process schematically illustrated in FIG. 4. The disclosed manufacturing sequence may however be altered by for example attaching the second sheet 72 to the first sheet 71 before folding a portion of the first sheet 71 around the leg elastic feature 17 to form a folded edge 73, as shown in FIG. 17.

Moreover, according to still a further design variation, the second sheet 72 may have a smaller width 77 in the longitudinal direction y than the width 79 of the entire first portion 3 in a finished state, i.e. after completed manufacturing, as schematically illustrated in FIG. 18. In the illustrated example embodiment of FIG. 18 the width 77 of the second sheet 72 is selected such that a gap 78 in the longitudinal direction y is formed between the edge 75 of the first sheet 71 and the lower edge 82 of the second sheet 72. The purpose of the second sheet 72 is mainly for covering any elastic feature of the front portion 3, and if the first sheet 71 itself is used for covering the leg elastic feature there is less reason for extending the second sheet 72 all the distance down to the folded edge, as shown in FIG. 16c or 17. Instead, the second sheet 72 may be located in the region of the first portion 3 having previously uncovered elastic feature, such as for example a belly region of the front portion 3, and/or a region of a waist elastic feature of the front portion 3. Further variations in width 77 of the second sheet 72 are possible. For example, the width 77 of the second sheet may be selected to extend down to the edge 75 of the first sheet 71 but without overlapping the folded portion 74.

In the example embodiment of FIG. 15 the absorbent article comprises front and back portions 3, 4 that are made of individual parts, and that are mutually interconnected by means of the absorbent body 5. The folded edge 73 at the leg edge 9, 10 is substantially parallel with the transverse direction x. However, variations in the shape and configuration are possible.

Figure 19:
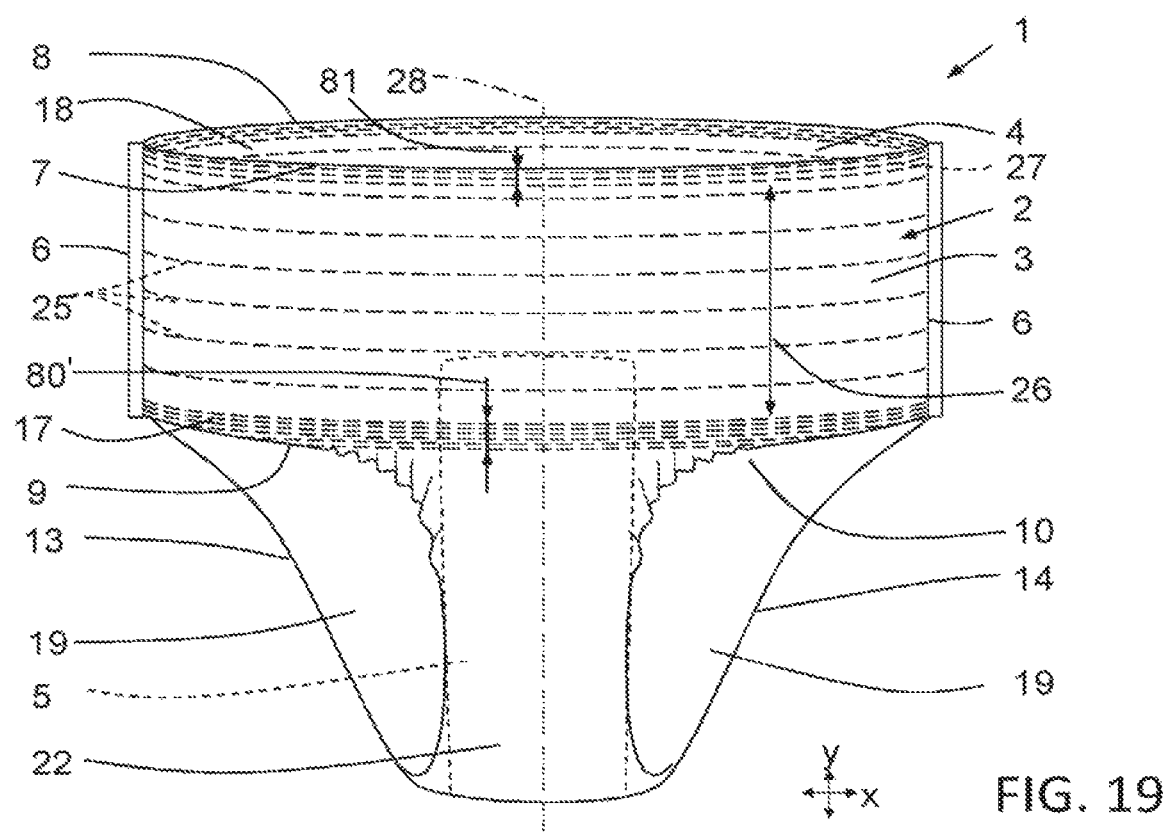
FIG. 19 shows a gender specific absorbent article.
Figure 20:
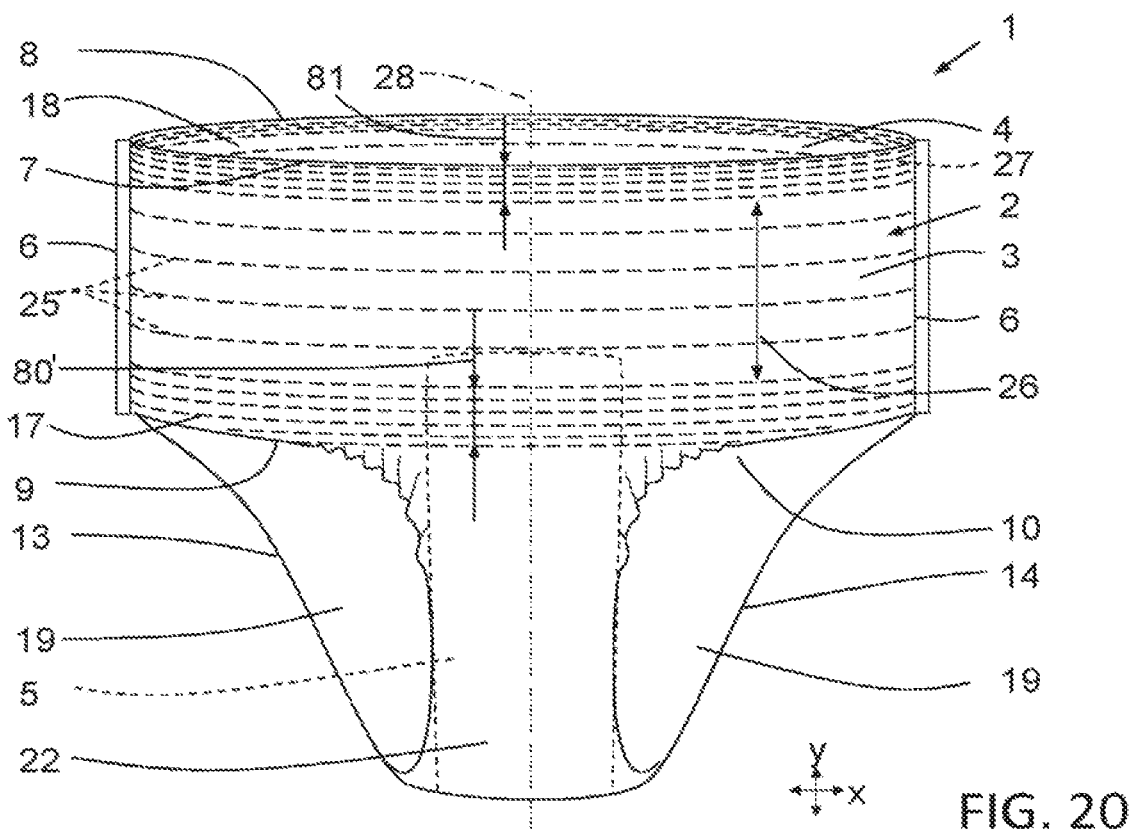
FIG. 20 shows a further gender specific absorbent article.

FIG. 19 and FIG. 20 illustrate how a specific absorbent article may be adapted to better fit a specific gender, such as female or male. FIG. 19 may for example illustrate a female article and FIG. 20 may represent a male article. By for example providing an absorbent article 1 adapted for a female with an elastic leg feature 17 that has a smaller width 80' than a corresponding width 80' of a male article 1, a better comfort and fit may be realised. Similarly, by for example providing an absorbent article 1 adapted for a female with an elastic waist feature 27 that has a smaller width 81 than a corresponding width 81 of a male article 1, a better comfort and fit may be realised.

Furthermore, it is also possible to have articles in which several parameters adapted to the specific gender. For example, an absorbent article 1 adapted for a female may be provide with an elastic leg feature 17 that has a smaller width 80' than a corresponding width 80' of a male article 1, and an elastic waist feature 27 that has a smaller width 81 than a corresponding width 81 of a male article 1. The combination of a specific elastic leg feature and specific elastic waist feature for each gender enables a better comfort and fit.

Any of the illustrated and disclosed example embodiments of the absorbent article according to the disclosure may be provided with a flat-front design. Flat-front design herein refers to a design of the absorbent article where at least a portion of the elastic feature extending in a substantially transverse direction x over the front portion is interrupted in a front region of the front portion. For example, a front region 21 is illustrated in FIG. 2 by means of a dash-dot-dot-dash line. The front region 21 is here depicted as extending over a portion of the absorbent body 5 and up towards the waist edge 7 of the front portion 3. The elastic feature within the front region 21, such as the elastic feature 25 in the centre region 26, the elastic leg feature 17 and/or elastic waist feature 27, may be unconnected to the at least one sheet of web material making up the front portion 3, such that the any elastic feature 25, 17, 27 within the front region 21 may snap back to natural, un-stretched, state when said elastic feature 25, 17, 27 is cut or made to break along the transverse sides 21a of the front region 21. The cutting or breaking of the elastic feature 25, 17, 27 along the transverse sides 21a of the front region 21 may for example be performed with a suitable machine during the manufacturing of the absorbent article 1. The removal of the gathering effect otherwise caused by the elastic feature 25, 17, 27 within the front region 21 results in a more smooth and flat appearance of the front region 21 of the absorbent article, which is desirable for providing the user with a more cloth-like undergarment appearance and the associated sense of comfort.

By "absorbent article" is meant an article that absorbs or is adapted to absorb bodily fluids, such as urine and/or blood.

The nonwoven material layers or webs of the present invention forming the chassis may for example be selected from, for example, of spunbond, air laid, wet laid, carded, electro spunned or meltblown nonwovens. The nonwoven material may be bonded by multiple techniques, e.g. by needling, hydroentangling, or heat bonding.

The nonwoven material of the disclosed products is a mixture of natural and synthetic materials. Natural fibres are for instance cellulosic fibres or fibres from regenerated cellulose.

The term "elastic thread" is intended to mean an elastic strand or elastic thread which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The threads may be of the elastane type that is available under the trade name "LYCRA", but any suitable elastic thread may be used. The threads may have a linear mass density, dtex, of about 80-1200 dtex.

The elastic threads are elongated during the production process from about 50 to about 300% of the initial, non-tensioned original length, more preferably 100-250% and most preferably 150-220% of the initial, non-tensioned original length. The elastic threads should preferably be of a type that are able to tolerate an elongation of at least about 200% without breaking, so that they can be safely used in the production process without risk for breaking.

Further information with respect to material about the elastic web material is disclosed in WO2014098683 A1, which is referred to in its entirety.

The absorbent body may comprise any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like.

The absorbent body may have a liquid permeable topsheet placed on the side intended to face the skin of a user, and a liquid impermeable backsheet placed on the side of the absorbent body intended to face the garment of a user. Generally, the liquid permeable topsheet comprises or consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent body, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. A disposable pant-type absorbent article comprising:
   a chassis; and
   an absorbent body;
   wherein the chassis has a front portion and a back portion, each of the front and back portions has a waist edge, a pair of leg edges and a pair of side edges;
   wherein the front and back portions are joined to each other at opposite ones of the pair of side edges to at least partly define a waist opening and a pair of leg openings, wherein the absorbent body is located mainly in a crotch portion of the article, wherein an elastic leg feature is fastened to the chassis at least partly along the leg edges in the front portion, wherein said article has a longitudinal direction and a transverse direction, wherein the elastic leg feature extends from the side edges towards a centre line extending in the longitudinal direction of the article, wherein a width in the longitudinal direction of the elastic leg feature is from 8 to 40 millimetres, as measured in an extended state of the absorbent article, wherein the elastic leg feature comprises a set of 4 to 10 individual elastic threads extending in the transverse direction, wherein at least one individual elastic thread of the elastic leg feature is at least 3 centimetres shorter than another individual elastic thread of said elastic leg feature, as measured in an extended state of the absorbent article, and a center region comprising individual elastic threads extending in the transverse direction is adjacent the elastic leg feature in the front portion, wherein a spacing in the longitudinal direction between adjacent ones of the individual elastic threads in the center region is greater than a spacing in the longitudinal direction between adjacent ones of the individual elastic threads n the elastic leg feature, wherein a portion of the elastic leg feature starting from one of the side edges has a first length that is at least 55% of a maximal length of the adjacent leg opening in the transverse direction, as measured in an extended state of the absorbent articleand vuithin an entirety of the portion of the elastic leg feature, the leg elastic feature is less than 6 millimetres from the leg edge in the longitudinal direction.

2. The pant-type absorbent article according to claim 1, wherein the elastic leg feature comprises a set of 4 to 8 individual elastic threads.

3. The pant-type absorbent article according to claim 2, wherein at least a significant portion of the individual elastic threads of the elastic leg feature are placed parallel to each other and with a gap of 1 to 6 millimetres between neighbouring threads, as measured in an extended state of the absorbent article.

4. The pant-type absorbent article according claim 3, wherein a number of individual elastic threads of the elastic leg feature varies along a length of the elastic leg feature.

5. The pant-type absorbent article according to claim 2, wherein at least one individual elastic thread of the elastic leg feature is cut off during cutting of the leg edge of the chassis.

6. The pant-type absorbent article according to claim 1, wherein the elastic leg feature comprises an elastic band.

7. The pant-type absorbent article according to claim 6, wherein at least part of the elastic band is cut off during cutting of the leg edge of the chassis.

8. The pant-type absorbent article according to claim 1, wherein an elastic waist feature is fastened to the chassis along the waist edge of the front and back portions, the elastic waist feature of the front and back portions extends in a transverse direction substantially parallel with each waist edge.

9. The pant-type absorbent article according to claim 8, wherein at least the front portion in a region of the waist edge and/or the leg edge has a stronger elasticity than in a centre region between the waist edge and the leg edge.

10. The pant-type absorbent article according to claim 1, wherein the first length is at least 5 centimetres in the transverse direction, starting from the side edge, as measured in an extended state of the absorbent article.

11. The pant-type absorbent article according to claim 1, wherein the first length is at least 60% of the maximal length of the leg opening in the transverse direction, as measured in an extended state of the absorbent article.

12. The pant-type absorbent article according to claim 1, wherein the absorbent article comprises a second length, which is defined by the maximal length in the transverse direction from the side edge to a point along the periphery of the leg edge having a cut leg elastic feature, wherein the second length is at least 30% of the maximal length of the leg opening in the transverse direction, as measured in an extended state of the absorbent article.

13. The pant-type absorbent article according to claim 1, wherein a direction of orientation of the elastic leg feature deviates less than 30 degrees from the transverse direction over an entire length of the elastic leg feature, as measured in an extended state of the absorbent article.

14. The pant-type absorbent article according to claim 1, wherein a direction of orientation of the elastic leg feature in the front portion deviates less than 7 degrees from the transverse direction over an entire length of the elastic leg feature, as measured in an extended state of the absorbent article.

15. The pant-type absorbent article according to claim 1, wherein the width of the elastic leg feature varies along the length of the elastic leg feature, as measured in an extended state of the absorbent article.

16. The pant-type absorbent article according to claim 1, wherein at least the front and/or back portion is extensively made of an elastic web material, wherein the elastic web material is made of at least two substantially inelastic sheets of web material that are laminated together and having an elastic feature sandwiched between said at least two sheets of web material, and wherein the elastic feature is attached to the at least two sheets in a tensioned state in the transverse direction to provide a web material that is elasticized in the transverse direction.

17. The pant-type absorbent article according to claim 1, wherein the chassis is cut such that an initial direction of orientation of the leg edge, starting from the side edge, deviates from the transverse direction towards the closest waist edge, such that an acute angle between the longitudinal direction and the initial direction of orientation of the leg edge near the side edge is formed, as measured in an extended state of the absorbent article.

18. The pant-type absorbent article according to claim 1, wherein a length of the leg edge in the longitudinal direction is less than 50% of a length of the leg edge in the transverse direction.

19. The pant-type absorbent article according to claim 1, wherein the leg edge is located at the front portion of the absorbent article.

20. A method for manufacturing a disposable pant-type absorbent article in a continuous process, the method comprising:

forming a chassis from at least one continuous web material, the chassis has a front portion and a back portion, each of the front and back portions has a waist edge, a pair of leg edges, a pair of side edges, wherein an elastic leg feature is fastened to the chassis at least partly along the leg edges, the elastic leg feature extends from the side edges towards a centre line in a longitudinal direction of the article, the elastic leg feature having a width in the longitudinal direction from 8 to 40 millimetres, as measured in an extended state of the absorbent article and comprises a set of 4 to 10 individual elastic threads extending in the transverse direction, wherein at least one individual elastic thread of the elastic leg feature is at least 3 centimetres shorter than another individual elastic thread of said elastic leg feature, as measured in an extended state of the absorbent article, the chassis further comprising a center region comprising individual elastic threads extending in the transverse direction and which is adjacent to the elastic leg feature in the front portion, wherein a spacing in the longitudinal direction between adjacent ones of the individual elastic threads in the center region is greater than a spacing in the longitudinal direction between adjacent ones of the individual elastic threads in the elastic leg feature, wherein a portion of the leg elastic feature starting from one of the side edges has a first length that is at least 55% of a maximal length of the adjacent leg opening in a transverse direction, as measured in an extended state of the absorbent article, and within an entirety of the portion of the elastic leg feature, the leg elastic feature is less than 6 millimetres from the leg edge, in a longitudinal direction, joining an absorbent body to the chassis such as to be located mainly in a crotch portion of the article; and joining the front and back portions to each other at opposite side edges to at least partly define a wrist-opening and a pair of leg openings.

21. The method according to claim 20, further comprising forming the chassis by means of cutting away pieces of the web material, wherein part of the elastic leg feature is cut away simultaneously with cutting of the leg edge of the chassis.

* * * * *